US012582330B2

(12) United States Patent
Kumar et al.

(10) Patent No.: US 12,582,330 B2
(45) Date of Patent: Mar. 24, 2026

(54) SYSTEMS AND METHODS FOR COMPUTER-ASSISTED SHAPE MEASUREMENTS IN VIDEO

(71) Applicant: KALIBER LABS INC., San Francisco, CA (US)

(72) Inventors: Bipul Kumar, San Francisco, CA (US); Mathew Francis, San Francisco, CA (US); Gaurav Yadav, San Francisco, CA (US); Biswajit Dev Sarma, San Francisco, CA (US); Tim Bakhishev, San Francisco, CA (US); Chandra Jonelagadda, San Francisco, CA (US); Mark Ruiz, San Francisco, CA (US); Ray Rahman, San Francisco, CA (US)

(73) Assignee: Kaliber Labs Inc., San Francisco, CA (US)

( * ) Notice: Subject to any disclaimer, the term of this patent is extended or adjusted under 35 U.S.C. 154(b) by 719 days.

(21) Appl. No.: 17/996,217

(22) PCT Filed: Apr. 13, 2021

(86) PCT No.: PCT/US2021/026986
§ 371 (c)(1),
(2) Date: Oct. 13, 2022

(87) PCT Pub. No.: WO2021/211516
PCT Pub. Date: Oct. 21, 2021

(65) Prior Publication Data
US 2023/0190136 A1 Jun. 22, 2023

Related U.S. Application Data

(60) Provisional application No. 63/143,390, filed on Jan. 29, 2021, provisional application No. 63/030,731, filed on May 27, 2020.

(30) Foreign Application Priority Data
Apr. 13, 2020 (IN) .............................. 202041015992

(51) Int. Cl.
*A61B 5/107* (2006.01)
*A61B 1/317* (2006.01)
(Continued)

(52) U.S. Cl.
CPC ............ *A61B 5/1076* (2013.01); *A61B 1/317* (2013.01); *A61B 5/0035* (2013.01);
(Continued)

(58) Field of Classification Search
CPC ..... A61B 5/1076; A61B 1/317; A61B 5/0035; A61B 5/1079; A61B 6/466; A61B 90/361;
(Continued)

(56) References Cited

U.S. PATENT DOCUMENTS 4,600,005 A 7/1986 Hendel
5,215,095 A 6/1993 Macvicar et al.
(Continued)

FOREIGN PATENT DOCUMENTS

EP 2194836 B1 11/2015
JP 2002065585 A 3/2002
(Continued)

OTHER PUBLICATIONS

Jonelagadda et al. U.S. Appl. No. 18/843,235 entitled "Arthroscopic surgery assistance apparatus and method," filed Aug. 30, 2024.
(Continued)

*Primary Examiner* — Siamak Harandi
(74) *Attorney, Agent, or Firm* — Shay Glenn LLP

(57) ABSTRACT
Various embodiments of the invention provide systems and methods to assist or guide an arthroscopic surgery (e.g.,
(Continued)

surgery of the shoulder, knee, hip or spine) or other surgical procedure by providing measurements intraoperatively. The systems and methods comprise steps of receiving a video stream from an arthroscopic imaging device; receiving one or more sets of coordinates of one or more points, paths, or area; calculating a length, a surface area, or a volume measurement based at least in part on the one or more sets of coordinates; overlaying the selected one or more sets of coordinates and the measurement on the video stream or on an expanded view of a region of surgery; and displaying the overlay on one or more display devices intraoperatively so as to be used by an operator during the arthroscopic procedure.

20 Claims, 10 Drawing Sheets

(51) Int. Cl.

| | | |
|---|---|---|
| *A61B 5/00* | (2006.01) | |
| *A61B 6/46* | (2024.01) | |
| *A61B 90/00* | (2016.01) | |
| *G06T 7/00* | (2017.01) | |
| *G06T 7/62* | (2017.01) | |
| *G16H 30/40* | (2018.01) | |

(52) U.S. Cl.
CPC ............ *A61B 5/1079* (2013.01); *A61B 6/466* (2013.01); *A61B 90/361* (2016.02); *G06T 7/0012* (2013.01); *G06T 7/62* (2017.01); *G16H 30/40* (2018.01); *G06T 2207/10081* (2013.01); *G06T 2207/10088* (2013.01); *G06T 2207/10132* (2013.01); *G06T 2207/20084* (2013.01)

(58) Field of Classification Search
CPC ........ A61B 1/000094; A61B 1/000096; A61B 1/0005; A61B 1/00193; A61B 6/487; A61B 8/466; A61B 34/25; A61B 2017/00203; A61B 2017/00207; A61B 2090/365; A61B 2090/371; A61B 2090/374; A61B 2090/3762; A61B 2090/378; A61B 6/032; A61B 6/037; A61B 6/12; A61B 6/461; A61B 6/486; A61B 6/5205; A61B 8/0841; A61B 8/461; A61B 8/5207; A61B 8/5223; A61B 6/5217; A61B 5/0036; A61B 5/0084; A61B 5/061; A61B 2576/00; A61B 90/06; A61B 5/055; A61B 2034/2065; A61B 2090/061; G06T 7/0012; G06T 7/62; G06T 2207/10081; G06T 2207/10088; G06T 2207/10132; G06T 2207/20084; G06T 2207/10068; G06T 2207/20081; G06T 2207/30096; G06T 2207/10016; G06T 2207/20101; G06T 2207/20221; G06T 2207/30004; G16H 30/40; G16H 20/40; G16H 30/20; G16H 40/63; G16H 50/20; G16H 50/70; G01R 33/5608
See application file for complete search history.

(56) References Cited

U.S. PATENT DOCUMENTS

| | | | |
|---|---|---|---|
| 6,491,699 B1 | 12/2002 | Henderson et al. | |
| 8,860,757 B2 | 10/2014 | Duhamel et al. | |
| 9,075,899 B1 | 7/2015 | Reicher | |
| 10,130,429 B1 | 11/2018 | Weir | |
| 10,169,535 B2 | 1/2019 | Mentis | |
| 10,543,046 B2 | 1/2020 | Charron et al. | |
| 10,806,325 B2 | 10/2020 | Miller et al. | |
| 11,832,996 B2 | 12/2023 | Shelton et al. | |
| 2003/0181810 A1 | 9/2003 | Murphy et al. | |
| 2003/0195883 A1 | 10/2003 | Mojsilovic et al. | |
| 2004/0087852 A1 | 5/2004 | Chen | |
| 2004/0199404 A1 | 10/2004 | Ripperger et al. | |
| 2006/0058616 A1 | 3/2006 | Marquart et al. | |
| 2006/0258938 A1 | 11/2006 | Hoffman et al. | |
| 2007/0016009 A1 | 1/2007 | Lakin et al. | |
| 2007/0116036 A1 | 5/2007 | Moore | |
| 2007/0168461 A1 | 7/2007 | Moore | |
| 2009/0088897 A1 | 4/2009 | Zhao et al. | |
| 2009/0317002 A1 | 12/2009 | Dien | |
| 2010/0249507 A1 | 9/2010 | Prisco et al. | |
| 2011/0190774 A1 | 8/2011 | Nikolchev et al. | |
| 2011/0202370 A1 | 8/2011 | Green, III et al. | |
| 2011/0301447 A1 | 12/2011 | Park et al. | |
| 2012/0130258 A1 | 5/2012 | Taylor et al. | |
| 2012/0226150 A1 | 9/2012 | Balicki et al. | |
| 2012/0289782 A1 | 11/2012 | Viola | |
| 2013/0073310 A1 | 3/2013 | Awdeh | |
| 2013/0096373 A1 | 4/2013 | Chabanas et al. | |
| 2013/0211232 A1 | 8/2013 | Murphy et al. | |
| 2014/0058406 A1 | 2/2014 | Tsekos | |
| 2014/0149407 A1 | 5/2014 | Qian et al. | |
| 2014/0216966 A1 | 8/2014 | Ramkhelawan et al. | |
| 2014/0236159 A1 | 8/2014 | Haider et al. | |
| 2014/0267658 A1 | 9/2014 | Speier et al. | |
| 2015/0005622 A1 | 1/2015 | Zhao et al. | |
| 2015/0161802 A1 | 6/2015 | Christiansen | |
| 2015/0221105 A1 | 8/2015 | Tripathi et al. | |
| 2015/0332196 A1 | 11/2015 | Stiller et al. | |
| 2016/0000515 A1 | 1/2016 | Sela et al. | |
| 2016/0151117 A1 | 6/2016 | Gibbs et al. | |
| 2016/0259888 A1 | 9/2016 | Liu et al. | |
| 2016/0270641 A1 | 9/2016 | Mirza et al. | |
| 2016/0378861 A1 | 12/2016 | Eledath et al. | |
| 2017/0007327 A1 | 1/2017 | Haider et al. | |
| 2017/0060867 A1 | 3/2017 | Moutinho | |
| 2017/0151022 A1 | 6/2017 | Jascob et al. | |
| 2017/0193160 A1 | 7/2017 | Long et al. | |
| 2018/0049622 A1 | 2/2018 | Ryan et al. | |
| 2018/0071032 A1 | 3/2018 | de Almeida Barreto | |
| 2018/0122506 A1 | 5/2018 | Grantcharov et al. | |
| 2018/0168740 A1 | 6/2018 | Ryan et al. | |
| 2018/0204111 A1 | 7/2018 | Zadeh et al. | |
| 2018/0247128 A1 | 8/2018 | Alvi et al. | |
| 2018/0249888 A1 | 9/2018 | Kucharski et al. | |
| 2018/0366231 A1 | 12/2018 | Wolf et al. | |
| 2018/0368656 A1 | 12/2018 | Austin et al. | |
| 2019/0069957 A1* | 3/2019 | Barral | A61B 34/20 |
| 2019/0192232 A1 | 6/2019 | Altmann et al. | |
| 2019/0209080 A1 | 7/2019 | Gullotti et al. | |
| 2019/0311493 A1 | 10/2019 | Hillborg | |
| 2019/0362834 A1 | 11/2019 | Venkataraman et al. | |
| 2019/0380792 A1 | 12/2019 | Poltaretskyi et al. | |
| 2019/0385302 A1 | 12/2019 | Ngo Dinh et al. | |
| 2020/0005949 A1 | 1/2020 | Warkentine | |
| 2020/0078123 A1 | 3/2020 | Venkataraman et al. | |
| 2020/0107002 A1 | 4/2020 | Casas | |
| 2020/0111564 A1 | 4/2020 | Mastros | |
| 2020/0197098 A1 | 6/2020 | Chopra et al. | |
| 2020/0210769 A1 | 7/2020 | Hou et al. | |
| 2020/0211720 A1 | 7/2020 | Goldberg | |
| 2020/0237452 A1 | 7/2020 | Wolf et al. | |
| 2020/0265273 A1 | 8/2020 | Wei et al. | |
| 2020/0273575 A1 | 8/2020 | Wolf et al. | |
| 2020/0394499 A1 | 12/2020 | Yao et al. | |
| 2021/0059758 A1 | 3/2021 | Avendi et al. | |
| 2021/0128244 A1 | 5/2021 | Couture et al. | |
| 2021/0192759 A1 | 6/2021 | Lang | |
| 2021/0196382 A1 | 7/2021 | Mumaw et al. | |
| 2021/0196398 A1 | 7/2021 | Ye et al. | |
| 2021/0256719 A1 | 8/2021 | Hufford et al. | |
| 2021/0298869 A1* | 9/2021 | Wolf | G16H 50/20 |
| 2021/0307841 A1 | 10/2021 | Buch et al. | |

(56) References Cited

U.S. PATENT DOCUMENTS

| | | |
|---|---|---|
| 2021/0327567 A1 | 10/2021 | Fine et al. |
| 2021/0338331 A1 | 11/2021 | Quaid, III |
| 2021/0338342 A1 | 11/2021 | Abhari et al. |
| 2022/0031402 A1 | 2/2022 | Ye |
| 2022/0079675 A1 | 3/2022 | Lang |
| 2022/0087746 A1 | 3/2022 | Lang |
| 2022/0104694 A1 | 4/2022 | Shelton, IV et al. |
| 2022/0122263 A1 | 4/2022 | Yang |
| 2022/0165403 A1 | 5/2022 | Asselmann et al. |
| 2022/0207896 A1 | 6/2022 | Fouts et al. |
| 2022/0287676 A1 | 9/2022 | Steines et al. |
| 2022/0406061 A1† | 12/2022 | Quist |
| 2023/0005266 A1† | 1/2023 | Quist |
| 2023/0029224 A1† | 1/2023 | Quist |
| 2023/0263573 A1 | 8/2023 | Bakhishev et al. |
| 2023/0298336 A1 | 9/2023 | Ghezelghieh et al. |
| 2023/0368398 A1 | 11/2023 | Figueroa-Alvarez et al. |
| 2023/0386074 A1 | 11/2023 | Canton et al. |
| 2024/0082019 A1 | 3/2024 | Jonelagadda |
| 2024/0415580 A1 | 12/2024 | Barban et al. |

FOREIGN PATENT DOCUMENTS

| | | |
|---|---|---|
| JP | 2013509273 | 3/2013 |
| JP | 2013513462 A | 4/2013 |
| JP | 2016506260 A | 3/2016 |
| JP | 2018537155 A | 12/2018 |
| JP | 2019508072 A | 3/2019 |
| KR | 10-1049507 B1 | 7/2011 |
| WO | WO00/64367 A1 | 11/2000 |
| WO | WO2004/095359 A2 | 11/2004 |
| WO | WO2017002388 A1 | 1/2017 |
| WO | WO2019/049503 A1 | 3/2019 |
| WO | WO2019/050612 A1 | 3/2019 |
| WO | WO2019/133071 A1 | 7/2019 |
| WO | WO2020/017212 A1 | 1/2020 |
| WO | WO2020035852 A2 | 2/2020 |
| WO | WO2020/047051 A1 | 3/2020 |
| WO | WO2021/144230 A1 | 7/2021 |
| WO | WO2021/263174 A1 | 12/2021 |
| WO | WO2022/197550 A1 | 9/2022 |
| WO | WO2022/221341 A1 | 10/2022 |
| WO | WO2022/221342 A1 | 10/2022 |
| WO | WO2022/249190 A1 | 12/2022 |

OTHER PUBLICATIONS

Jonelagadda et al. U.S. Appl. No. 18/864,893 entitled "Surgery evidence report generation," filed Nov. 11, 2024.

Buslaev et al.; Albumentations: Fast and flexible image augmentations; Information; 11(2); 125; doi: 10.33990/info11020125; 20 pages; Feb. 2020.

Kumar et al.; U.S. Appl. No. 17/918,873 entitled "Systems and methods for ai-assisted surgery," filed Oct. 13, 2022.

Kumar et al.; U.S. Appl. No. 17/996,212 entitled "Systems and methods of computer-assisted landmark or fiducial placement in videos," filed Oct. 13, 2022.

Petscharnig et al.; Binary convolutional neural network features off-the-shelf for image to video linking in endoscopic multimedia databases; Multimedia Tools and Applications; 77(21); pp. 28817-28842; Nov. 2018.

Petscharnig; Semi-automatic retrieval of relevant segments from laparoscopic surgery videos; InProceedings of the 2017 ACM on International Conference on Multimedia Retrieval; pp. 484-488; Jun. 6, 2017.

Schoeffmann et al.; Content-based retrieval in videos from laparoscopic surgery; InMedical Imaging 2016: Image-Guided Procedures, Robotic Interventions, and Modeling; SPIE; vol. 9786; pp. 562-571; Mar. 18, 2016.

Wei et al.; Real-time visual servoing for laparoscopic surgery; Controlling robot motion with color image segmentation; IEEE Engineering in Medicine and Biology Magazine: 16(1); pp. 40-45; Jan. 1997.

Stallmo et al.; U.S. Appl. No. 18/878,669 entitled "Surgical analytics and tools," filed Dec. 24, 2024.

Jonelagadda et al.; U.S. Appl. No. 19/127,410 entitled "Apparatus and method for interactive three-dimensional surgical guidance," filed May 5, 2025.

Jonelagadda et al.; U.S. Appl. No. 19/101,587 entitled "System and methods for surgical collaboration," filed Feb. 5, 2025.

Hertel; Trust and Behavioral Intention Toward Generative Adversarial Network (GAN)-Derived Avatar Healthcare Provider (HCP) in Simulated Telehealth Setting. The Florida State University; 2021; retrieved from the internet (https://diginole.lib.fsu.edu/islandora/object/fsu:803248/datastream/PDF/view); on Nov. 3, 2023.

Jonelagadda et al.; U.S. Appl. No. 18/692,794 entitled "System and method for searching and presenting surgical images," filed Mar. 15, 2024.

Jonelagadda et al.; U.S. Appl. No. 18/693,945 entitled "System and method for computer-assisted surgery," filed Mar. 20, 2024.

Jonelagadda; U.S. Appl. No. 18/637,440 entitled Systems and methods for using image analysis in superior capsule reconstruction,f filed Apr. 16, 2024.

Antico et al.; Deep learning-based femoral cartilage automatic segmentation in ultrasound imaging for guidance in robotic knee arthroscopy; Ultrasound in medicine & biology; 46(2); pp. 422-435; Nov. 22, 2019.

Jonmohamadi et al.; Automatic segmentation of multiple structures in knee arthroscopy using deep learning; IEEE Access; vol. 8; pp. 51853-51861; Mar. 10, 2002.

Cheng et al.; Deep learning assisted robotic magnetic anchored and guided endoscope for real-time instrument tracking; IEEE Robotics and Automation Letters, 6(2); pp. 3979-3986; Mar. 17, 2021.

Demirel; A hierarchical task analysis of shoulder arthroscopy for a virtual arthroscopic tear diagnosis and evaluation platform (VATDEP); The International Journal of Medical Robotics and Computer Assisted Surgery; 13(3):e1799;29 pages; (Author Manuscript); Sep. 2017.

Jung et al.; Navigation-assisted anchor insertion in shoulder arthroscopy: a validity study; BMC Musculoskeletal Disorders; 21(1); pp. 1-9; Dec. 2020.

Ruiz U.S. Appl. No. 18/555,248 entitled "Systems and methods for AI-assisted medical image annotation," filed Oct. 12, 2023.

Mourgues et al.; Interactive guidance by image overlay in robot assisted coronary artery bypass. InInternational Conference on Medical Image Computing and Computer-Assisted Intervention; Berlin, Heidelberg: Springer Berlin Heidelberg; pp. 173-181; Nov. 15, 2003.

Winne et al.; Overlay visualization in endoscopic ENT surgery; International journal of computer assisted radiology and surgery; 6(3); pp. 401-406; May 2011.

* cited by examiner
† cited by third party bluDot Registration and Tracking System Overview

205

202

204

201

203

701

SYSTEMS AND METHODS FOR COMPUTER-ASSISTED SHAPE MEASUREMENTS IN VIDEO

CROSS REFERENCE TO RELATED APPLICATIONS

This PCT application claims the benefit of priority to Indian Provisional Patent Application No. 202041015992, filed Apr. 13, 2020, and U.S. Provisional Patent Application Nos. 63/030,731, filed May 27, 2020, and 63/143,390, filed Jan. 29, 2021, the contents of all of which are fully incorporated herein by reference for all purposes.

BACKGROUND

Field of the Invention Embodiments of the invention relates to systems, devices, and methods for assisting with surgical procedures, particularly using Artificial Intelligence (AI).

In recent years, Artificial Intelligence has begun to be developed to be used to process images to recognize features of a human face as well as different anatomical structures in a human body. These AI tools can be used to automatically recognize an anatomical feature or pathology to assist an operator during a medical procedure. Computational methods such as machine learning and deep learning algorithms can be used for image or language processing to gather and process information generated during a medical procedure. The hope is to use AI algorithms to improve the outcome of the surgery. However, current AI-assisted surgical systems and methods are still less than ideal in many respects, for example, in guiding a surgical procedure. Accordingly, improved AI-assisted surgical systems and methods are desired.

BRIEF DESCRIPTION OF THE INVENTION

Various embodiments of the invention provide computer-implemented medical systems, devices, and methods to guide a surgical procedure including for example various minimally invasive procedures such as arthroscopic procedures. Various embodiments of the invention provide such guidance by identifying and labelling anatomical features and pathology in real-time and estimating dimensional (e.g., length, width), surface, or volumetric measurements. Surgeons use measurements such as a distance between points or features, a shape, a surface area, or a volume of feature to, for example, place grafts or remove a portion of a tissue or bone based on such measurements. To remove an accurate portion of the tissue or the bone or to place a graft properly the surgeon requires dependable measurements during a surgery. A surgeon may attempt to make a measurement using a conventional tool such as a ruler, but in some instances the area may not be easily reachable by a ruler or a conventional measurement device. In some instances, using a physical measurement device may be invasive and pose a risk during a surgery. Therefore, computer-implemented medical systems, devices, and methods such as Artificial Intelligence (AI) tools, particularly for guiding medical procedures by estimating measurements (e.g., length, surface area, or volumetric) can be valuable. These AI tools can have their limitations in accurately and reliably predicting a tool, anatomical structure, a pathology and reliably estimating a measurement. In a fast-paced surgical procedure, the AI tool may need to also make predictions with low latency to provide real time assistance to an operator.

Recognized herein is the need for fast, accurate and reliable AI tools to assist an operator in real time during the course of a surgical procedure by estimating a shape of a feature and/or a measurement (e.g., length, surface area, or volume). Accordingly, aspects of the present invention provide a pipeline of machine learning algorithms that is versatile and well trained for one more of shape estimation and making measurements within a surgical field in various medical procedures including various minimally invasive procedures such as arthroscopic, endoscopic, laparoscopic, cardioscopic and related procedures. Examples of such minimally invasive procedures can include one or more of Arthroscopic procedures (e.g., repair of a torn rotator cuff in the shoulder, ACL surgery of the knee, repair of various non-arthritic hip disorders, repair of damaged cartilage in the ankle or removal of bone spurs in the ankle); Gastro-intestinal (GI) procedures (e.g., biopsy of the intestines, removal of polyps, bariatric surgery, stomach stapling/vertical banded gastroplasty), urological procedures (e.g., removal of kidney stone, bladder repair), gynecological procedures (e.g., a dnc, removal or other treatment of uterine fibroids, etc.) and a laparoscopic procedures (e.g., an appendectomy, cholecystectomy, colectomy, hernia repair, nissen fundoplication).

Embodiments of the invention described herein provide systems, devices, and methods that can receive information (e.g., image, voice, user inputs) prior to and during a medical procedure (e.g., a surgery), process the received information to identify features associated with a measurement or shape estimation, and provide a measurement or shape estimation for points or features of interest in real time during the procedure.

Aspects of the present invention also aid surgeons with a measurement or shape estimation for points or features of interest intraoperatively by using images acquired preoperatively using various imaging modalities such as magnetic resonance imaging (MRI) including function MRI, computed tomography (CT) scanning, positron emission tomography (PET) scanning or ultrasound imaging with still other imaging modalities contemplated. The preoperative images may contain one or more surgical fields of view. Artificial Intelligence (AI) can be applied to the preoperative images to overlay the images and/or location of points or features of interest (e.g., a pathology such as a torn rotator cuff, torn/frayed tendon, a polyp or a tumor) onto a real-time video stream of a surgical procedure to provide guidance to a surgeon. We refer to AI modules/algorithms used intraoperatively, preoperatively, or postoperatively to assist with the surgical procedure or improve an outcome of the procedure as Surgical AI.

One aspect of the present invention provides a system for guiding an arthroscopic procedure such as a repair to a shoulder, knee, hip, ankle or other joint. Application of embodiments of the system to the guidance of other medical procedures including minimally invasive procedures such as endoscopic, laparoscopic, and interventional cardiovascular procedures is also contemplated. In some embodiments, the system comprises one or more computer processors and one or more non-transitory computer-readable storage media storing instructions that are operable, when executed by the one or more computer processors, to cause the one or more computer processors to perform operations comprising: receiving a video stream captured by an imaging device; processing the video stream using at least one of a trained computer algorithm; receiving an indication from an operator to select one or more of a plurality of points or an area in the video stream; calculating one or more measurements for the selected area in the video stream; and displaying the measurements on a displaying device intraoperatively to be used by an operator during the arthroscopic procedure. In some embodiments, the processing comprises: (i) identifying one or more elements in the video stream, where the one or more elements comprise one or more of an anatomical structure, a surgical tool, an operational procedure or action, or a pathology; and (ii) labeling the identified elements in the video stream. In some embodiments, the one or more measurements comprise one or more of a length, a surface area, a circumference, or a volume.

In various embodiments, the arthroscopic procedure is an arthroscopic surgery such as a repair to a shoulder, knee, hip, elbow, ankle, foot or hand. In various embodiments, the imaging device may correspond to or more of an arthroscope, endoscope, laparoscope or cardioscope one or more of which may be configured as an interventional imaging device. Also, embodiments of the system can be configured to process a video stream from the imaging device that is monocular or stereoscopic and relatedly embodiments of the system can be configured to make adjustment for changes from monocular to stereoscopic views during the course of a surgical other medical procedure.

In some embodiments, the trained computer algorithm comprises one or more trained machine learning algorithms, one or more trained deep learning algorithms, or a combination of both.

In some embodiments, the processing the video stream further comprises one or more processing modules from a list of modules including one or more of: a video stream decomposition module, a tool recognition module, a tooltip reference sizing module, an anatomy recognition module, a tool tracking module, a gesture recognition module, a landmark establishment module, a distance aggregator module, a video blend module, a pathology detection module, a pathology sizing module, or a radiology imaging module. In some embodiments, the one or more processing modules comprise one or more trained machine learning algorithms. In some embodiments, the trained machine learning algorithm is a neural network. In some embodiments, the video stream decomposition module decomposes the video stream into a series of images. Also, in some embodiments, the series of images are stored in a memory device.

In some embodiments, the tooltip reference sizing module estimates a size of a tooltip of the identified surgical tool using a trained machine learning algorithm. In some embodiments, the pathology sizing module estimates a size of the identified pathology (e.g., the size of a tissue tear or size of a tumor) based at least partially on the estimated size of the tooltip.

In some embodiments, the radiological imaging module comprises: a radiology ingest module, a three-dimensional image construction module, a visual field mapping module, a real-time volume computation module. In some embodiments, the radiology ingest module interfaces with an external repository of images to import a subject's radiological imagery. In some embodiments, the radiological imagery comprises one or more of magnetic resonance imaging (MRI), computed tomography (CT) scanning, positron emission tomography (PET) scanning, ultrasound, or a combination thereof. In some embodiments, the radiological imagery includes an image of a landmark. In some embodiments, the radiological imagery comprises volumetric data.

In some embodiments, a three-dimensional image reconstruction module generates a three-dimensional object (e.g., a shoulder joint) from the volumetric radiological imagery. In some embodiments, the three-dimensional object is saved in a memory device. In some embodiments, the three-dimensional image reconstruction module further generates coordinates to map one or more landmarks onto the three-dimensional object.

In some embodiments, the labeling the video stream further comprises displaying a shape outline surrounding the one or more elements. In some embodiments, the operator uses a standard surgical probe to select the area in the video stream. In some embodiments, the plurality of points in the video stream comprises two or more points. In some embodiments, calculating the one or more measurements comprises calculating a distance between a first point and a second point. In some embodiments, calculating one or more measurements comprises detecting the first point and the second point in a field of view of the video stream. In some embodiments, the at least one of the first point or the second point moves outside of the field of view. In some embodiments, the second point is a location on at least one element of the one or more elements in the video stream closest to the surgical probe tip at a time of measurement. In some embodiments, a distance between the first point and the second point is substantially continuously measured and displayed.

In some embodiments, calculating the one or more measurements for the selected area comprises performing a volume calculation e.g., for all or a portion of the selected area. In some embodiments, the volume calculation comprises: receiving a three dimensional radiology image of a subject; receiving an indication from an operator to select at least one element from the one or more elements in the video stream; and calculating a volume of the selected area based at least partially on the selected at least one element on the three dimensional radiological image.

In some embodiments, receiving the indication of the operator to select the at least one element from the or more elements in the video stream comprises receiving an outline of a selected area from the operator. In some embodiments, the volume is calculated based on the received outline from the operator. In some embodiments, the calculating one or more measurements is used in a superior capsule reconstruction procedure. In some embodiments, the calculating one or more measurements is used for bone-loss estimation.

In some embodiments, the operations further comprise generating an overlay video stream by blending the labels or the measurements with the received video stream; and displaying the overlaid video stream on a displaying device.

Another aspect of the present invention provides computer-implemented methods for guiding an arthroscopic procedure such as a repair to a shoulder, knee, hip, ankle or other joint. Application of embodiments of the system to the guidance of other medical procedures including various minimally invasive procedures such as endoscopic, laparoscopic and interventional cardiovascular procedures is also contemplated. In some embodiments, the methods comprise: receiving a video stream captured by an imaging device; processing the video stream using at least one of a trained computer algorithm; receiving an indication from an operator to select one or more of a plurality of points or an area in the video stream; calculating one or more measurements for the selected area in the video stream; and display the measurements on a displaying device intraoperatively to be used by an operator during the arthroscopic procedure. In some embodiments, the one or more measurements comprise one or more of a length, a surface area, a circumference, or a volume. In some embodiments, the processing comprises: (i) identifying one or more elements in the video stream; and (ii) labeling the identified elements in the video stream. In some embodiments, the one or more elements comprise one or more of an anatomical structure, a surgical tool, an operational procedure or action, or a pathology.

In some embodiments, the arthroscopic procedure is an arthroscopic surgery. In some embodiments, the imaging device is an interventional device. In some embodiments, the video stream is monocular. In some embodiments, the video stream is stereoscopic. In some embodiments, the imaging device is one or more of an arthroscope, though in others, it may correspond to one or more of a cardioscope, endoscope or laparoscope.

In some embodiments, the trained computer algorithm comprises one or more trained machine learning algorithms, one or more trained deep learning algorithms, or a combination of both.

In some embodiments, the processing of the video stream further comprises one or more processing modules from a list of modules including one or more of: a video stream decomposition module, a tool recognition module, a tooltip reference sizing module, an anatomy recognition module, a tool tracking module, a gesture recognition module, a landmark establishment module, a distance aggregator module, a video blend module, a pathology detection module, a pathology sizing module, or a radiology imaging module. In some embodiments, the one or more processing modules comprise one or more trained machine learning algorithms. In some embodiments, the trained machine learning algorithm is a neural network. In some embodiments, the video stream decomposition module decomposes the video stream into a series of images. In some embodiments, the series of images are stored in a memory device.

In some embodiments, the tooltip reference sizing module estimates a size of tooltip of the identified surgical tool using a trained machine learning algorithm. In some embodiments, the pathology sizing module estimates a size of the identified pathology based at least partially on the estimated size of tooltip.

In some embodiments, the radiological imaging module comprises: a radiology ingest module, a three-dimensional image construction module, a visual field mapping module, a real-time volume computation module. In some embodiments, the radiology ingest module interfaces with an external repository to import a subject's radiological imagery. In some embodiments, the radiological imagery comprises one or more of MRI, CT scans, PET scan, ultrasound, or a combination thereof. In some embodiments, the radiological imagery includes an image of a landmark. In some embodiments, the radiological imagery comprises a volumetric data. In some embodiments, the three-dimensional image reconstruction module generates a three-dimensional object from the volumetric radiological imagery. In some embodiments, the three-dimensional object is saved in a memory device. In some embodiments, the three-dimensional image reconstruction module further generates coordinates to map the landmark onto the three-dimensional object.

In some embodiments, the labeling the video stream further comprises displaying a shape outline surrounding the one or more elements. In some embodiments, the operator uses a standard surgical probe to select the area in the video stream. In some embodiments, the plurality of points in the video stream comprises two or more points. In some embodiments, calculating one or more measurements comprises calculating a distance between a first point and a second point. In some embodiments, the first point and the second point are detectable in a field of view of the video stream. In some embodiments, the least one of the first point or the second point moves outside of the field of view. In some embodiments, the second point is a location on at least one element of the one or more elements in the video stream closest to the surgical probe tip at a time of measurement.

In some embodiments, a distance between the first point and the second point is substantially continuously measured and displayed. In some embodiments, calculating the one or more measurements for the selected area comprises performing a volume calculation. In some embodiments, the volume calculation comprises: receiving a three dimensional radiology image of a subject; receiving an indication from an operator to select at least one element from the one or more elements in the video stream; and calculating a volume of the selected area based at least partially on the selected at least one element on the three dimensional radiological image. In some embodiments, receiving the indication of the operator to select at least one element from the or more elements in the video stream comprises receiving an outline of a selected area from the operator. In some embodiments, the volume is calculated based on the received outline from the operator. In some embodiments, calculating one or more measurements is used in a superior capsule reconstruction procedure. In some embodiments, calculating one or more measurements is used for bone-loss estimation.

In some embodiments, the methods further comprise generating an overlay video stream by blending the labels or the measurements with the received video stream; and displaying the overlaid video stream on a displaying device.

Another aspect of the present invention provides computer-implemented methods for expanding a field of view in a surgical video stream such as that from arthroscopic, endoscopic, laparoscopic or other real-time imaged surgical procedure. In some embodiments, the methods comprise: receiving a video stream captured by an imaging device; decomposing the video stream into a one or more images; processing the one or more images using at least one of a trained computer algorithm to (i) extract one or more image features, (ii) identify one or more anatomical structures; and generating a composite image to expand the field of view by matching the one or more images based on the extracted features or the identified anatomical structures.

In some embodiments, the interventional imaging device is an endoscope. In some embodiments, the surgical video stream is an endoscopic surgery video stream. In some embodiments, the endoscopic surgery is one or more of arthroscopic surgery, GI surgery, gynecological surgery or urological surgery. In various embodiments, the video stream can be or stereoscopic and the system can be configured to process images from either as well as switch between the two during the course of a medical procedure. In some embodiments, the one or more image features comprise one or more sets of distinct pixels. In some embodiments, the distinct pixels contain distinct colors. In some embodiments, the trained computer algorithm comprises one or more trained machine learning algorithms, one or more trained deep learning algorithms, or a combination of both. In some embodiments, a distance, a surface area, or a volume can be measured using the composite image.

Another aspect of the present invention provides a non-transitory computer readable medium comprising machine executable code that, upon execution by one or more computer processors, implements any of the methods above or described elsewhere herein.

Another aspect of the present invention provides a system comprising one or more computer processors and computer memory coupled thereto. The computer memory comprises machine executable code that, upon execution by the one or more computer processors, implements any of the methods above or described elsewhere herein.

Additional aspects and advantages of embodiments of the present invention will become readily apparent to those skilled in this art from the following detailed description, wherein only illustrative embodiments of the present invention are shown and described. As will be realized, the present invention is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the invention contained in the specification, the specification is intended to supersede and/or take precedence over any such contradictory material.

BRIEF DESCRIPTION OF THE DRAWINGS

The novel features of embodiments of the present invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
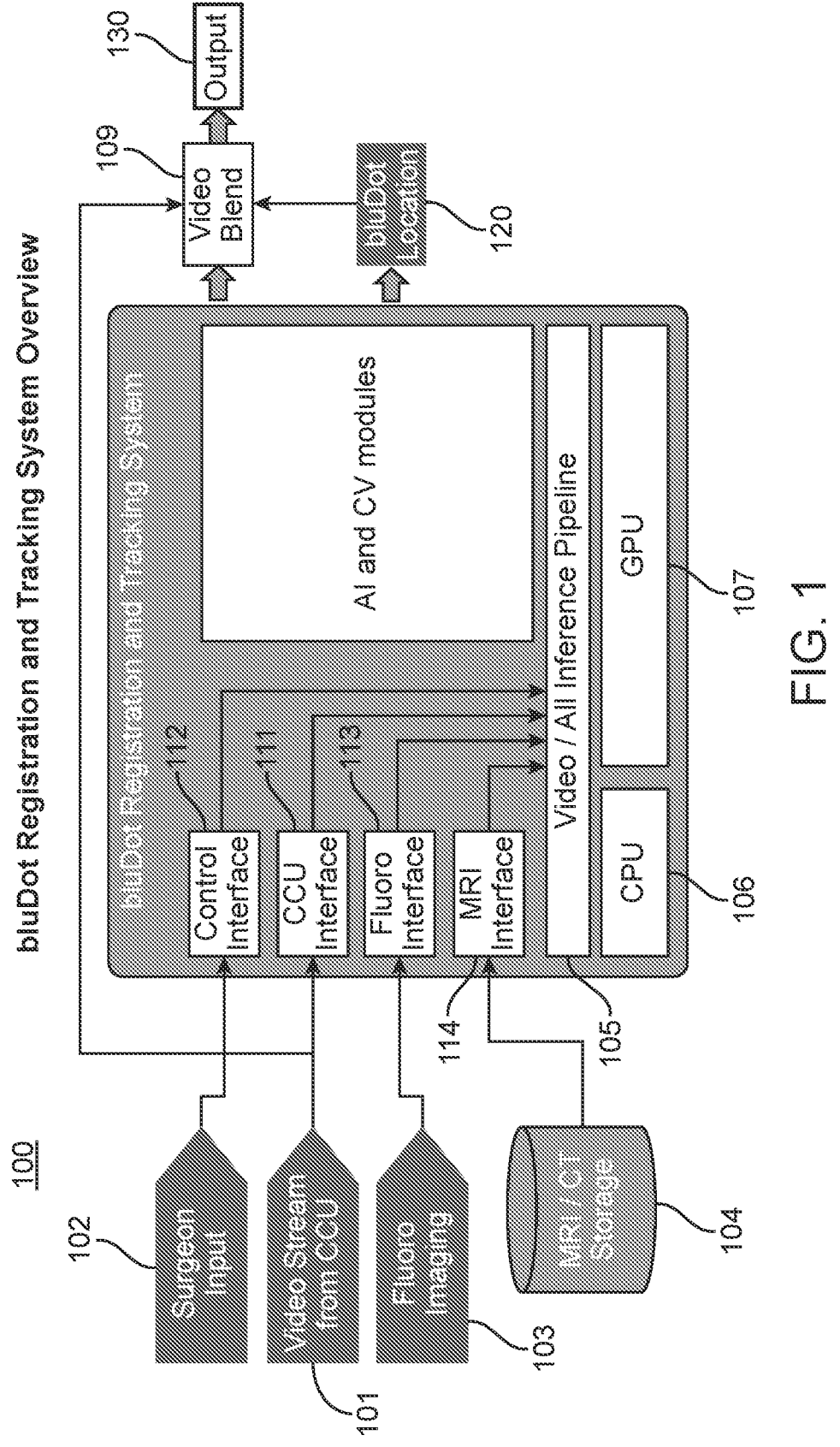
FIG. 1 shows schematic example of a hardware configuration of a system for assisting an arthroscopic procedure, according to some embodiments.

While various embodiments of the present invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Various embodiments of the present invention provide computer-implemented medical systems, devices, and methods for assisting surgeons in an intraoperative setting using AI. The systems, devices, and methods disclosed herein may improve upon existing methods of shape estimation and assessing measurements in a surgical field of view by providing a fast and reliable classification (e.g., real-time) of various elements involved in a surgical operation (e.g., surgical tools, anatomical features, or a pathology) and estimating a shape or assessing measurements (e.g., length, surface area, or volumetric) with high precision and accuracy based on the classification of various elements. For example, systems, devices, and methods provided herein may use AI methods (e.g., machine learning, deep learning) to build a classifier which improves a real-time classification of elements involved in a surgical operation and identifies a location of a landmark by intraoperative command from an operator (e.g., using a surgical probe) or by processing preoperative medical images (e.g., on MRI, or CT scan), where the preoperative medical images contains locations of interest in an area of surgery (e.g., a landmark). An AI approach may leverage large datasets in order gain new insights from the datasets. The classifier model may improve real-time characterization of various elements involved in an operation which may lead to higher operation success rate. The classifier model may provide an operator (e.g., surgeon, operating room nurse, surgical technician) with information for more accurate measurements which eliminates the shortcomings of physical measurements. The measurement and shape estimation are dynamic, removeable, or traceable by using an input from a user (e.g., a button press or a foot pedal press). The measurement(s) may not inhibit physical movement of the surgical tools during the surgery as opposed to using conventional measurement tools e.g., a ruler). The measurements may be performed using a tool (e.g., a tool tip) that is being used in the surgery. The systems and methods here can overlay a measurement or shape estimation on a video stream of the surgery on demand (e.g., to display or not display the measurement based on a command from an operator).

Reference will now be made in detail to various embodiments, examples of which are illustrated in the accompanying drawings. In the following detailed description, numerous specific details are set forth in order to provide a thorough understanding of the present invention and the described embodiments. However, the embodiments of the present invention are optionally practiced without these specific details. In other instances, well-known methods, procedures, components, and circuits have not been described in detail so as not to unnecessarily obscure aspects of the embodiments. In the drawings, like reference numbers designate like or similar steps or components.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items.

As used herein, the term "if" is optionally construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" is optionally construed to mean "upon determining" or "in response to determining" or "in accordance with a determination" or "upon detecting" or "in response to detecting" that the stated condition precedent is true, depending on the context.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, the terms "comprises," "comprising," or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, the terms "subject" and "patient" are used interchangeably. As used herein, the terms "subject" and "subjects" refers to a human being. In certain embodiments, the subject is going through a surgical operation. In certain embodiments, the subject is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "surgical AI" or "surgical AI module", as used herein, generally refer to a system, device, or method that uses Artificial Intelligence algorithms to assist before, during, and/or after a surgical operation. A surgical AI module can be defined as a combination of input data, machine learning or deep learning algorithms, training datasets, or other datasets.

The term "machine learning", as used herein, may generally refer to computer algorithms that can improve automatically over time. Any description herein of machine learning can be applied to Artificial Intelligence, and vice versa, or any combination thereof.

As used herein, the terms "continuous," "continuously" or any other variation thereof, generally refer to a substantially uninterrupted process or a process with time delay that is acceptable in the context of the process.

The terms "video stream," or "video feed", as used herein, refer to data generated by a digital camera. Video feed may be a sequence of static or moving pictures.

The terms "region," "organ," "tissue," "structure", as used herein, may generally refer to anatomical features of the human body. A region may be larger than an organ and may comprise an organ. An organ may comprise one or more tissue types and structures. A tissue may refer to a group of cells structurally joined to complete a common function. A structure can refer to a part of a tissue. In some embodiments, a structure may refer to one or more parts of one or more tissues joined together to create an anatomical feature.

The terms "surgical field of view," or "field of view," as used herein, refer to the extent of visibility captured by an interventional imaging device. Field of view may refer to the extent of visual data captured by a digital camera that is observable by human eye.

The term "decision," as described herein, may refer to outputs from a machine learning or AI algorithm. A decision may comprise labeling, classification, prediction, etc.

The term "interventional imaging device," as used herein, generally refers to an imaging device used for medical purposes. The interventional imaging device may refer to an imaging device that is used in a surgical operation. The surgical operation, in some embodiments, may be a simulation of an operation.

The term "operator," used herein, refers to a medical professional involved in a surgical operation. An operator can be a surgeon, an operating room nurse, a surgical technician.

The term "landmark", "arbitrary landmark", "virtual landmark", and "fiducial marker" are as used interchangeably herein to refer to marks used to guide surgical or other medical procedures.

An aspect of the invention provides a system for assisting an arthroscopic procedure by allowing computer-implemented arbitrary landmark placement. According to an embodiment, the system may comprise one or more computer processors and one or more non-transitory computer-readable storage media storing instructions that are operable, when executed by the one or more computer processors, to cause the one or more computer processors to perform operations comprising: receiving a video stream from an arthroscopic imaging device; receiving one or more sets of coordinates of one or more landmarks; overlaying the one or more landmarks on the video stream; and displaying the overlay on one or more display devices intraoperatively to be used by an operator during the arthroscopic procedure. In some embodiments, an operator (e.g., a surgeon) provides the one or more sets of coordinates of one or more landmarks preoperatively.

Another aspect of the invention provides a method for assisting an arthroscopic procedure. According to an embodiment, the system may comprise receiving a video stream captured by an imaging device; processing the video stream using at least one of a trained computer algorithm, wherein the processing comprises (i) identifying one or more elements in the video stream, wherein the one or more elements comprise one or more of an anatomical structure, a surgical tool, an operational procedure or action, or a pathology; and (ii) labeling said identified elements in the video stream. The method may further comprise receiving an indication from an operator to select one or more of a plurality of points or an area in the video stream; and display the measurements on a displaying device intraoperatively to be used by an operator during the arthroscopic procedure.

The video stream may be provided by the arthroscopic imaging device during the arthroscopic procedure. In some embodiments, the imaging device is or is incorporated into interventional device. In some embodiments, the arthroscopic imaging device comprises a digital camera. The video stream may be obtained from a digital camera specialized for an arthroscopic procedure. In various embodiments, the video stream may be monocular, stereoscopic be switchable between the two views or include a combination of video streams that are monocular and stereoscopic. The digital camera may be mounted on a rigid scope, suitable for work in the arthroscopic joints. The scope may comprise an optical fiber which illuminates a field of view of the surgery. The digital camera may be mounted to a camera control unit. In some embodiments, a camera control unit is configured to capture digital information produced by the digital camera. In some embodiments, the camera control unit converts the digital information produced by the digital camera into the video stream. In some embodiments, the camera control unit is configured to control a light source. In some embodiments, the camera control unit is configured to record the digital information produced by the digital camera in a memory device. In some embodiments, the memory device used to record the digital information is a local memory device, while in others it may be a remote device as described below. In some embodiments, the camera control unit is configured to overlay the output from the one or more computer processors with the video stream. In some embodiments, the memory device is a remote or cloud-based memory device. The camera control unit may send the video stream to the one or more computer processors. In some embodiments, there is more than one camera control unit. For example, in various embodiments, there are 2, 3, 4, 5, or more camera control units. The one or more camera control units may send the video streams to the computer processors via a network connection (which may be wireless) or a wired media connection. The video stream may be stereoscopic or monocular. In some embodiments, the system further comprises a display monitor. In some embodiments, the system comprises a mechanism to receive an input from the at least one operator (e.g., to activate or stop making a measurement or to estimate a shape) intraoperatively. In some embodiments, the mechanism receives the input via a push-button, a touchscreen device, a foot pedal, a gesture recognition system, or a voice recognition system.

In some embodiments, the one or more sets of coordinates are provided during the surgery using a digital pointer (e.g., a computer mouse or related device) that can mark an image in the video stream to select a point or a region of surgery. In some embodiments, an operator (e.g., a surgeon) provides the one or more sets of coordinates intraoperatively by indicating the desired location using a standard surgical probe. In some embodiments, after the coordinates of a desired location are selected or indicated, an operator can issue a command so the system can register the location. In some embodiments, the system receives the register command from the operator via a push-button, a touchscreen device, a foot pedal, a gesture recognition system, or a voice recognition system.

FIG. 1 shows a schematic example of a hardware configuration of an embodiment of the system described herein. The exemplary system 100 may comprise a plurality of inputs. In various embodiments, the plurality of inputs may comprise a video stream input 101, an operator (e.g., surgeon) input 102, and one or more preoperative imaging inputs. The preoperative imaging inputs may comprise a fluoroscopy imaging input 103, a medical data system (e.g., radiology imaging such as MRI, or CT scan) input 104. In some embodiments, each of the plurality of inputs is connected to a corresponding interface. For example, according to one or more embodiment, video stream input 101 is connected to a camera control unit (CCU) 111, surgeon input module 102 is connected to a control interface 112, fluoroscopy imaging input 103 is connected to a fluoroscopy interface 113, or imaging input 104 is connected to a medical data system (e.g., radiology imaging) interface 114. Each of the interfaces may be configured to receive an input from their corresponding inputs. The system 100 may support other external interfaces to receive input in various modalities from the surgeon, clinical data systems, surgical equipment, etc. The plurality of inputs received by a plurality of interfaces may then be sent to a processing unit to be processed using an artificial intelligence (AI) pipeline. In some embodiments, the processing unit may comprise a central processing unit (CPU) 106, a graphical processing unit (GPU) 107, or both. In some embodiments, a CPU or a GPU comprises a plurality of CPUs or GPUs. The CPU or GPU may be connected to the plurality of interfaces via a media connector (e.g., an HDMI cable, a DVI connector). The CPU or GPU may be connected to the plurality of interfaces (e.g., surgical video camera) over network connection (e.g., TCP/IP), which may provide more flexibility with less wired connections. In some embodiments, the latency in video processing and playback may be higher when the connection is via network as compared to a media connector. In some embodiments, the network connection may be a local network connection. The local network may be isolated including a set of predefined devices (e.g., devices being used in the surgery.) Lower latency may be more desirable for real-time feedback (e.g., during a surgery). In some embodiments, a system setup with higher latency can be used for training purposes (e.g., a mock surgery). The AI pipeline may comprise one or more machine learning modules or AI modules comprising one or more computer vision (CV) modules. In some embodiments, the AI and CV modules are supported by a video and AI inferencing pipeline (VAIP) 105. In some embodiments, VAIP 105 supports the AI and CV modules and manages the flow of control and information between the modules. VAIP 105 may comprise a configuration file comprising instructions for connecting and managing the flow. VAIP 105 may support execution of the AI algorithms on a GPU 107. VAIP 105 may also support direct media interfaces (e.g., HDMI, or DVI). One or more outputs 120 of the plurality of inputs processed by the AI pipeline may be generated comprising a shape estimation, a measurement (e.g., a distance, a surface area, or a volume), or a landmark location and one or more feature elements identified from the plurality of inputs or a video blend 109. The one or more outputs may be overlaid onto the video stream input 101 to generate an output 130. In some embodiments, the system 100 comprises a display monitor. In some embodiments, output 130 is displayed on a display monitor (e.g., a monitor, a television (TV)). In some embodiments, the system comprises a displaying device. In some embodiments, output 120 and video blend 109 are sent back to the CCU to be overlaid onto the video stream to generate 130.

In some embodiments, the arthroscope may generate consecutive images (e.g., a video feed) at a rate of at least about 10 frames per second (fps), though embodiments of the invention may be configured to input and process video feeds a smaller and larger number of frames per second. In some embodiments, the system may rest in between two consecutive frames from the video stream (e.g., video stream input 101) generating a latency in the system. In some embodiments, the latency in the system is at most 1/fps. In various embodiments, the latency of the system may also be less than the inverse of the rate of consecutive image generation of the surgical camera.

Figure 2A:
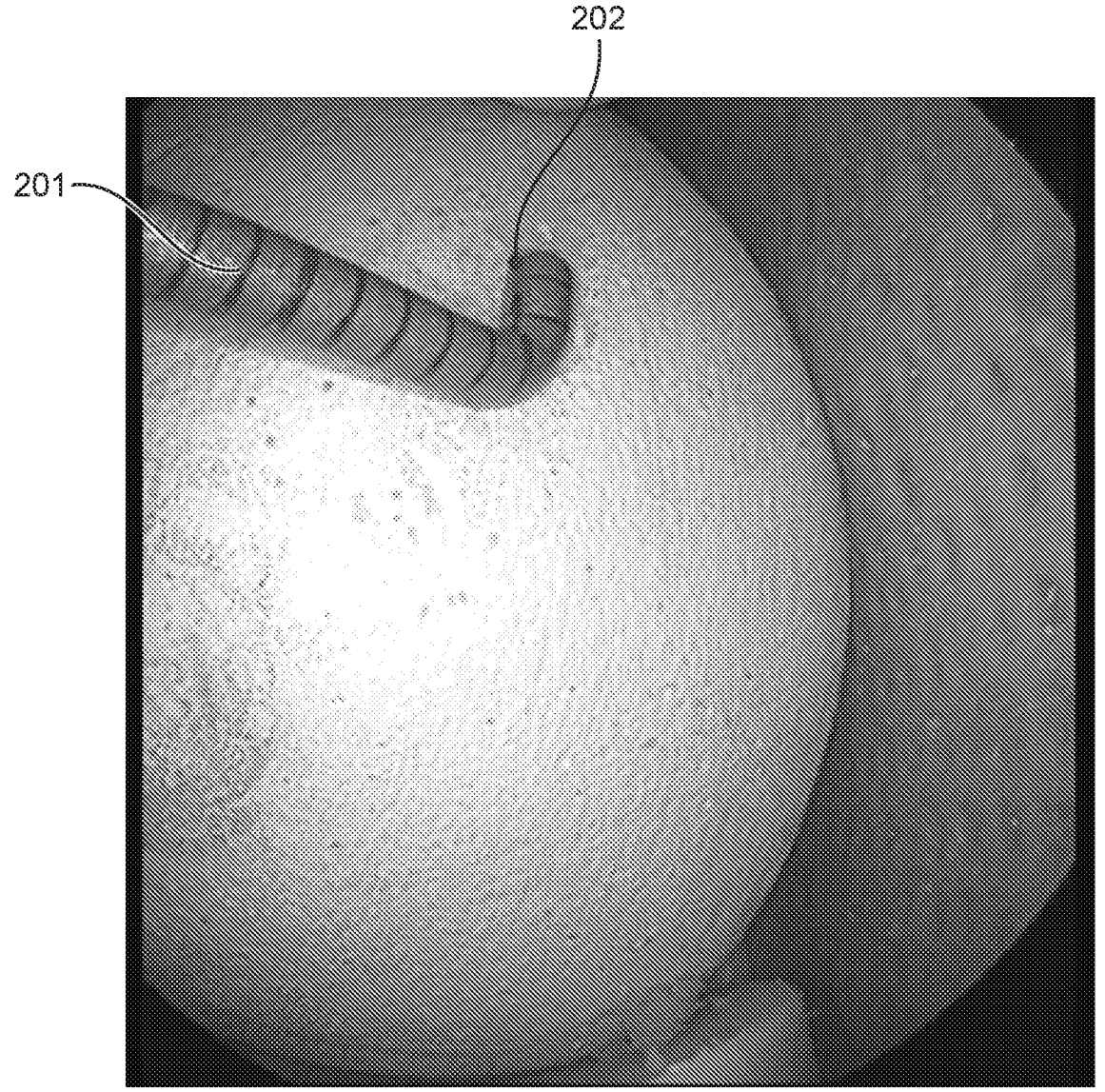
FIG. 2A shows an example of initiating a start location for a measurement using a probe, according to some embodiments.
Figure 2B:
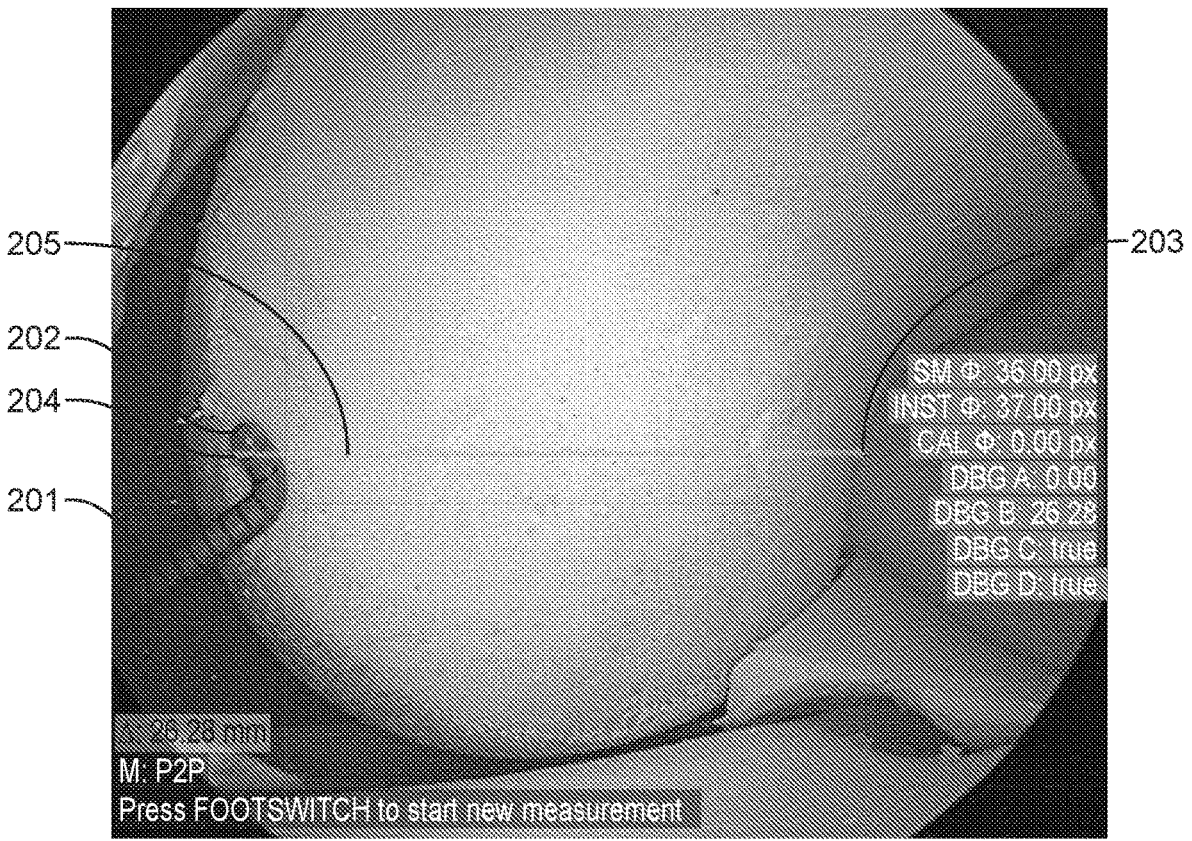
FIG. 2B shows an example of a point-to-point measurement, according to some embodiments.
Figure 2C:
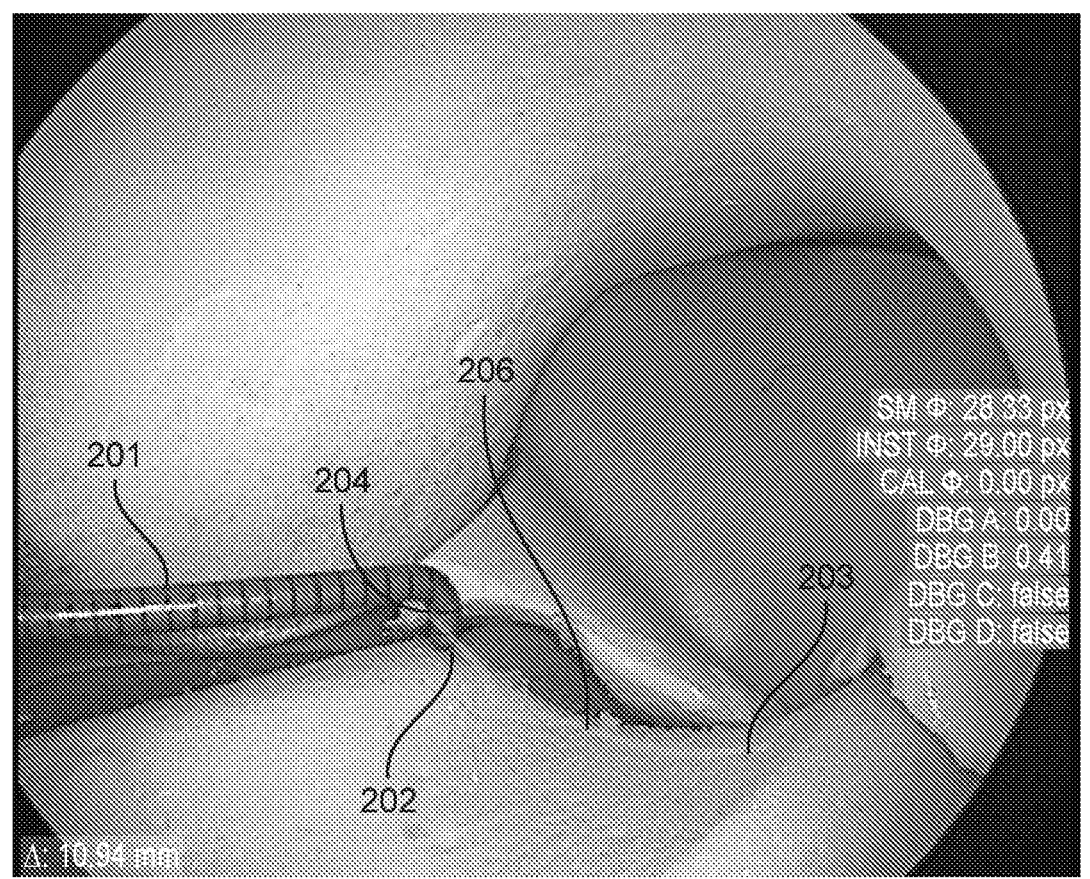
FIG. 2C shows an example of a curved point-to-point measurement, according to some embodiments.

In embodiments, the output 130 may comprise a point-to-point distance measurement. A standard surgical probe may be used to register a start location. In some embodiments, a size of the probe or a part thereof is known. The system may identify the probe and store a location of the probe. The point-to-point distance may then be calculated by aggregating a displacement of the probe location from a first point to a second point. The measurement of the point-to-point distance may be estimated based, at least in part on, the size of the probe and a location of the probe (e.g., the distance of the probe from the lens of a camera). FIG. 2A shows an example of a technique for initiating a start location for a measurement using an arbitrary probe 201. The probe and a tip 202 of the probe is recognized by the system. In some embodiments, the probe tip is used to select the start location. In such embodiments, an operator (e.g., a surgeon) may issue a command to register the start location. The command may be a gesture, a voice command, a mechanical button (e.g., a pedal), or a digital button (e.g., a button on a touch screen). The operator may then trace a path along a surface of one or more anatomical structures and stop at an end location. In some embodiments, the system computes the distance along the traced path between the start location and the end location. In some embodiments, the system outputs the measurement in suitable units, i.e., millimeters (mm), inches (in), etc. In some embodiments, the entire path is in the surgical field of view at all times. In some embodiments, the path is a curved path. In some embodiments, the path is a straight line. FIG. 2B shows an example of a point-to-point measurement between a start location 203 and an end location 204, with a traced line 205 that is straight. FIG. 2C shows an example of a point-to-point measurement, where the traced line 206 is curved. In some embodiments, the start location drops out of the camera's field of view as the camera pans away (e.g., following the probe). The system performs a point-to-point measurement when the start point falls outside of the field of view. In some embodiments, the start location and/or the end location are displayed on an expanded canvas. An expanded canvas may comprise the surgical field of views in different images acquired from the video stream that may be connected to one another to generate a larger field of view. In some embodiments, the probe operates on the virtually expanded field of view (or expanded canvas) assembled by compositing images from the camera when it pans the surgery area and its surroundings. In some embodiments, the operator (e.g., a surgeon) traces the outline of the anatomical structures. The system may then output an area of the traced region (e.g., a portion of an anatomical structure, or a pathology). In some embodiments, the system provides a measurement for the volume of the region traced by the operator. For example, the system may use preoperative inputs (e.g., MRI, or CT) to measure a volume of the portion of the anatomical structure or the pathology traced by the operator.

Figure 7A:
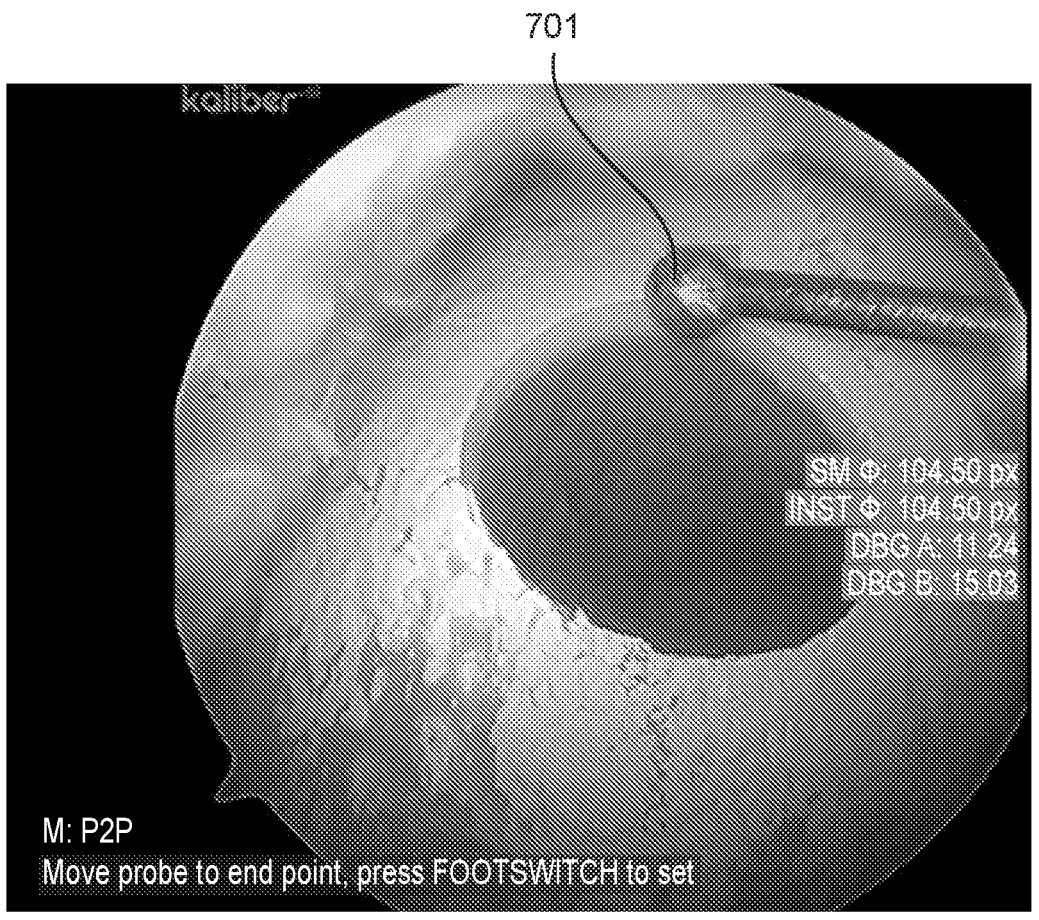
FIG. 7A shows an example of selecting a point for a point-to-point measurement, according to some embodiments.
Figure 7B:
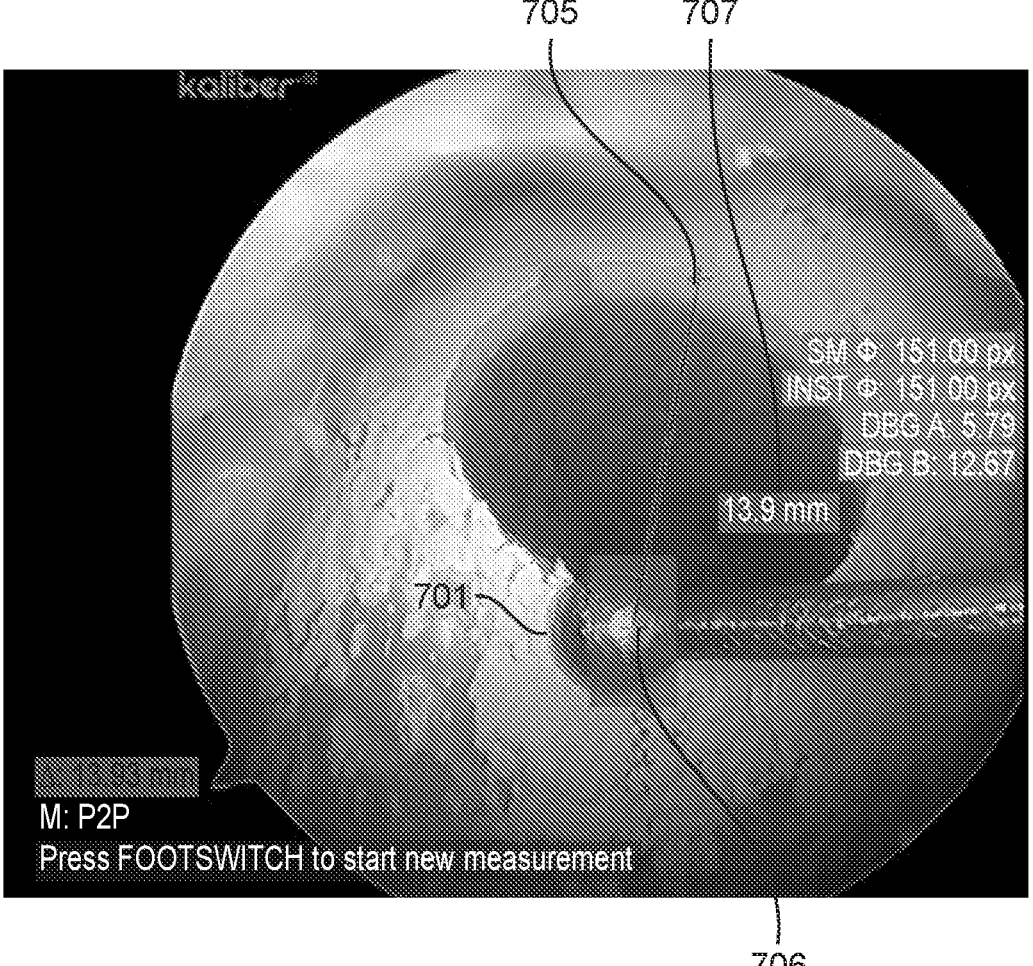
FIG. 7B shows an example of a point-to-point measurement, according to some embodiments.

Another example of performing a measurement comprising initiating a start location and an end location are provided in FIGS. 7A and 7B. A surgeon may mark a start location using a foot pedal or a button press (FIG. 7A). The system may recognize a tip of a probe 701 and registers a first location representing the start location. The surgeon may move the probe to another location and mark an end location using the foot pedal or button press. The system may recognize the probe head 701 and register a second location representing the end location. The system may then calculate a distance between the start and the end location. The start location 705, the end location 706 and the distance 707 may be visually outputted on a screen (FIG. 7B).

In some embodiments, an MRI image processed as described herein combined with tool tracking module 306 (FIG. 3) may provide the information required to estimate a size (e.g., a volume of a pathology (an injury or tumor, anatomy, or tissue). For example, imaging modalities (e.g., MRI) may produce images in which a voxel, (volumetric pixel), can represent a volume in physical space. Voxel sizes can range from about 0.5 to about 1.5 mm along two dimensions. A third dimension may be determined by the width of a slice which may be determined, for example, by the intended use of the MRI. Therefore, to map an MRI image, the anatomical structures may be matched in the MRI to those seen in the surgical field of view to determine the size of the anatomical structures. This measurement may be calculated partially based on the three dimensionality of the surgical field.

In some embodiments, the operations may further comprise identifying and labeling one or more elements in the video stream using at least one of a trained computer algorithm, where the one or more elements comprise one or more of an anatomical structure, a surgical tool, an operational procedure or action, or a pathology. In some embodiments, identifying and labeling the one or more elements in the video stream comprises using one or more AI modules. In some embodiments, the one or more AI module may comprise one or more modules for video stream decomposition, tool recognition, anatomy recognition, tool tracking, gesture recognition, point registration (e.g., a first location, an end location, line traced by an operator, etc.), or anatomy or landmark tracking.

In some embodiments, the arthroscopic procedure is an arthroscopic surgery. In some embodiments, the arthroscopic procedure is used in a rotator cuff repair surgery. In some embodiments, the arthroscopic procedure is used in an ACL repair in a knee surgery. In some embodiments, the arthroscopic procedure is used in a graft placement procedure. In some embodiments, the arthroscopic procedure is used in a decompression procedure. In some embodiments, the decompression procedure comprises removal or reshaping of bony structures to reduce pain. In some embodiments, a shoulder arthroscopic procedure comprises placement of a graft.

In some embodiments, the arthroscopic procedure comprise removal, or resection of an inflamed tissue and/or frayed tendons or cartilage. In some embodiments, the arthroscopic procedure is used in a removal of or a resection of one or more inflamed tissues. In some embodiments, the arthroscopic procedure is used in a removal of or a resection of one or more frayed tendons or cartilage where the video stream is monocular.

In some embodiments, the system 100 operates on stored video content of arthroscopic or other surgical or medical procedure. In these and related embodiments, a video recording of an arthroscopic surgery can be played back and sent to an interface. The system may then overlay any measurement or shape estimation on the video stream as explained herein. In some embodiments, displaying the measurement or shape estimation on a recording of a surgery is used for training purposes. In some embodiments, the system operates on stereoscopic video streams. In some embodiments, the system can be used during a robotic arthroscopic procedure (e.g., a surgery). In some embodiments, a view of the display may be changed. In some embodiments, by changing a view measurement or shape estimation that is overlaid on a video stream can be omitted from being displayed. In some embodiments, a change in the view is automatic. In some embodiments, changing a view may be cause by the AI pipeline identifying an anatomical structure or pathology.

Figure 3:
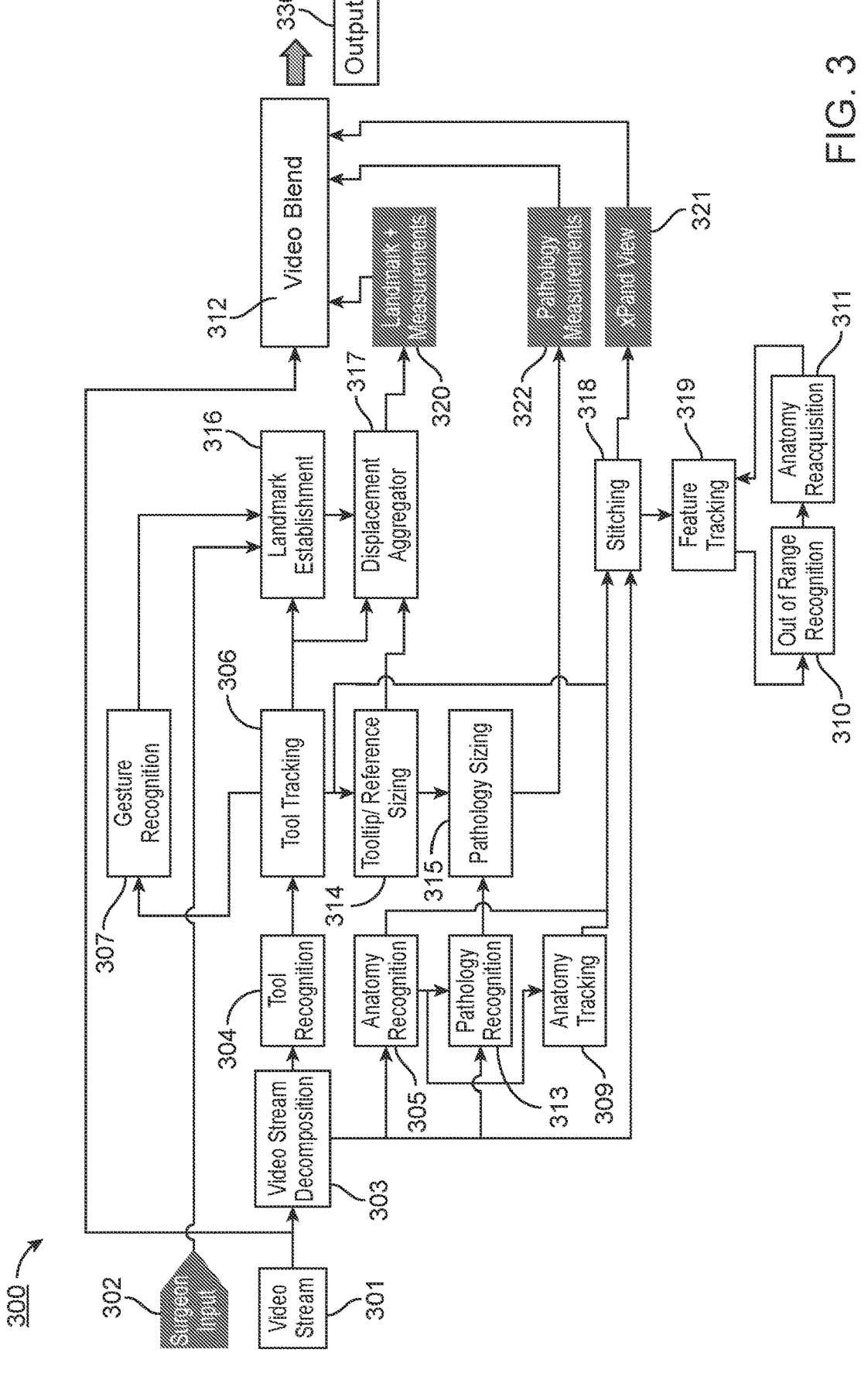
FIG. 3 shows a schematic of an exemplary flow chart of a method to perform a point-to-point measurement, according to some embodiments.

In some embodiments, a set of points or arbitrary paths are provided by an operator (e.g., a surgeon) intraoperatively. FIG. 3 shows a schematic of an exemplary flow chart of a measurement between arbitrary points or over an arbitrary path being performed in an arthroscopic procedure using a system 300. The system may comprise a plurality of modules which operate on the video stream input 301 generated by an arthroscopic camera and an input received from an operator 302 (e.g., a surgeon). In some cases, 301 is processed by a video stream decomposition module 303 comprising a CV algorithm to decompose a video stream into a series of images. The series of images may be stored in a memory device. One or more images from the series of images may be provided to one or more downstream component comprising a tool recognition module 304, an anatomy recognition module 305, a pathology recognition module 313, or a stitching module 318. In some cases, 303 outputs an image of the field of view of the surgery.

In some cases, the stitching module 318 may be used to provide a wider surgical view (e.g., a continues canvas). In some cases, when the endoscopic camera is moved by the operator, new objects and new regions of existing objects come into view. In order to generate a continuous canvas, the newly acquired frame may be evaluated against a previous frame. Distinctive visual features or feature points (e.g., anatomical features) may then be extracted from the previous frame and the new frame. The algorithms in the stitching module may track each feature to a new location in the next frame. Two or more frames may then be connected or stitched to one another by matching these feature points (e.g., boundaries of anatomical structures) to generate a wider surgical view (e.g., a continuous canvas). An operator or user may be able to navigate over the wider surgical view and have visual access to a surgical view that is wider than the surgical view provided by the camera.

In some cases, the tool recognition module 304 uses an AI network to recognize surgical tools in the field of view. Non-limiting examples of the AI network used in 304 may comprise Mask R-CNN, UNET, ResNET, YOLO, YOLO-2, or any combination thereof. In some cases, the AI networks are trained to recognize surgical tools of interest using a machine learning training comprising architecture-specific training techniques. In some cases, the trained AI network detects the presence of a surgical tool in an image and outputs a mask. The mask may be a set of pixels extracted from the input image, which indicate the precise outline of the surgical tool. In some casessome embodiments, the AI network outputs a box (e.g., a rectangular region) in which the tool is detected or displayed. The output from tool recognition module 304 is then sent to a tool tracking module 306. In some embodiments, tool tracking module 306 tracks a tool recognized in tool recognition module 304. In some embodiments, tool tracking module 306 detects new coordinates for the tool and stores the old coordinates of the tool in an array. In some embodiments, tool tracking module 306 provides information on a tool or probe (e.g., coordinates of a tool tip) to a reference sizing module 314.

In some embodiments, an output from tool recognition module 304 is provided to a tool tracking module 306. In some embodiments, the tool tracking module 306 tracks the motion of the one or more tools identified by the tool recognition module 304. In some embodiments, a position of a tool (e.g., an instantaneous position of the tool) may be stored in a memory (e.g., a buffer). In some embodiments, tool tracking module 306 uses CV algorithms to compute the velocity and acceleration of the tool and stores these values in the memory. This data may be stored as a fixed length array. In some embodiments, this array is stored in the time order that they were captured. In some embodiments, the array is stored in descending order of time. The array may have a fixed length and with adding new data, an older entry may be dropped out of the array and the memory buffer. In some embodiments, adding a new entry causes the oldest entry to be dropped out of the array. An output of the tool tracking module 306 may comprise the mask of the recognized tool along with the array of the tool's velocity and/or acceleration. The module 306 may supply a position or an array of the positions of one or more tool to a gesture recognition module 307 and a point registration (e.g., a first location, an end location, or a traced path) module 316.

In some embodiments, the anatomy recognition module 305 uses an AI network to recognize an anatomical structure in a field of view. Non-limiting examples of the AI network used in 305 may comprise Mask R-CNN, UNET, ResNET, YOLO, YOLO-2, or any combination thereof. In some embodiments, the AI networks are trained to recognize anatomical structures of interest using architecture-specific training techniques. In some embodiments, the trained AI network recognizes anatomical structures as they are sighted in the field of view. In some embodiments, the trained network outputs pixel masks, which may indicate the precise outline of the recognized anatomical structure. In some embodiments, the trained network outputs a box (e.g., a rectangular region) in which the anatomical structure was detected or is displayed. In some embodiments, anatomy recognition module 305 sends output of a recognized anatomical structure to pathology recognition module 313. In some embodiments, an output form pathology recognition module 313 is sent to anatomy tracking module 309 for tracking the recognized anatomical structure. In some embodiments, an anatomy mask from anatomy recognition module 305 is supplied to pathology recognition module 313. The mask may be treated as a region of interest and pathology recognition module 313 may confine itself to this region. In some embodiments, pathology recognition module 313 may interface with external modules for pathology recognition, for example, to recognize tumor, hernias, etc. A pathology of interest may comprise a defect in cartilage, rotator cuff tear, dislocated or torn labrum, torn ACL, anterior cruciate ligament, torn meniscus, torn bicep tendon, inflamed synovial tissue, or femoral acetabular impingement (FAI).

In some embodiments, the pathology recognition module 313 uses an AI network to recognize a pathology in a field of view. Non-limiting examples of the AI network used in pathology recognition module 313 may comprise Mask R-CNN, UNET, ResNET, YOLO, YOLO-2, or any combination thereof. In some embodiments, the AI networks are trained to recognize a pathology of interest using architecture-specific training techniques. In some embodiments, the trained AI network recognizes a pathology as it is sighted in the field of view. In some embodiments, the trained network outputs pixel masks, which may indicate the precise outline of the recognized pathology. In some embodiments, the trained network outputs a box (e.g., a rectangular region) in which the pathology was detected or is displayed. In some embodiments, an output from pathology recognition module 313 comprises a pathology mask defining an outline of a pathology and/or a size estimate of the pathology. In some embodiments, pathology recognition module 313 output of the recognized pathology is sent to a pathology sizing module 315. In some embodiments, pathology sizing module 315 uses information from reference sizing module 314 to compare the recognized pathology from pathology recognition module 313 with a tool tip from reference sizing module 314. In some embodiments, reference sizing module 314 uses AI networks to recognize the shape of the tip of the surgical tool used to perform the measurements. In some embodiments, the AI networks are trained using images of a surgical tool when viewed at different orientations, angles, illumination levels, or against different backgrounds. In some embodiments, the AI networks are trained to discern the intended location of a target point, given the orientation of the tool. Once the tip of the tool has been reliably sighted, the system may compute a size of the tip. This may be evaluated against the known size of the probe, as described herein. In some embodiments, the tool tip is constantly in motion and/or a plane of movement of the tool is not assumed to be orthogonal to an axis of the camera. Therefore, the system may repeat estimating the location of the tool tip continuously. In some embodiments, the reference sizing module 314 estimates a size of tooltip using a trained machine learning algorithm. In some embodiments, reference sizing module 314 provides a mask outlining the tip of the tool. For example, a portion of the tool (e.g., a left or right side of a probe head, or a tip of a tool) may be featured using a mask to visually a reference point used to mark a start point or an end point of a measurement. In some embodiments, reference sizing module 314 also provides a width of the tool in pixels. The width of the tool may be calibrated in the field of view. In some embodiments, pathology sizing module 315 uses the size of a probe or tool tip to estimate a size of the pathology recognized by pathology recognition module 313. The output from pathology sizing module 315 is then sent to pathology measurement module 322.

In some embodiments, the surgeon may automatically size a pathology (e.g., defect) using the pathology measurement module 322. The anatomical recognition 305 may first detect the anatomy on which the pathology is present. Then the pathology may be recognized by the pathology recognition module 313. Once an outline of the pathology has been recognized, the surgeon may be guided to place a reference tool (e.g., a surgical probe) in the field of view. The tool recognition module 304 may then detect the tool. A size of the pathology may then be computed based at least in part on the size of the tool using the pathology sizing module 315. In some embodiments, the pathology is not on a plane normal to the scope. In these cases, the tool may be placed at different locations near the pathology to estimate the size of the pathology more accurately. For example, if the defect is on a plane normal to the lens, the size of the tool, placed anywhere in the field of view in the same plane, can be used to directly measure the size of the pathology. In some other cases, the defect may not be on a plane which is normal to the lens. In these cases, the plane is first estimated. The plane may be estimated base at least in part on a perceived size of the tool. For example, when the perceived size of the tool remains the same when the tool is identified at different locations in the surgical images from a video stream, the plane of the anatomical structure or pathology in the images may be in a plane normal to the lens. In some embodiments, a tool is identified at least three different locations on an anatomical structure to estimate a plane of the anatomical structure or a pathology with respect to the lens. The size of the pathology may then be calculated using the tool size and the plane of the pathology.

In some embodiments, the gesture recognition module 307 uses an AI network comprising a memory (e.g., a recurrent neural network (RNN)), to interpret the movement of the tools. In some embodiments, the AI network is trained to recognize specific tools and/or identify specific movement patterns. For example, a tap would involve the tool moving in a specific manner relative to the background anatomy. In embodiments, the surgeon can indicate a position of an arbitrary point or path by using a predetermined gesture using a surgical tool. Non-limiting examples of a gesture may comprise tapping, double tapping, triple tapping, wagging (e.g., moving a tool from left to right). In some embodiments, gesture recognition module 307 outputs a label of the gesture made by an operator using a tool. In some embodiments, gesture recognition module 307 recognizes a gesture made by the operator and generates a label of the name of the recognized gesture to be supplied to a downstream component, which may be point registration module 316.

In some embodiments, the point registration module 316 receives one or more inputs from the operator 302, tool tracking module 306 and/or gesture recognition module 307, as shown in FIG. 3. In some embodiments, the input from gesture recognition module 307 instructs point registration module 316 that a gesture from an operator is recognized. The gesture may then be mapped to an action. In some embodiments, the mapping is configured preoperatively and is loaded from a database when the system is initialized. Non-limiting examples of an action mapped by point registration module 316 may comprise register start, register end, clear all, etc. In some embodiments, point registration module 316 is updated to interpret additional gestures and map them to various tasks. The register start action may comprise supplying a location of a tool to the displacement aggregator module 317, which may start a measurement process. The register end action may comprise trigger displacement aggregator module 317 to end the measurement process and/or to output a distance, a surface area or a volume. The clear all action may comprise clearing any measurement or masks displayed on a screen. In some embodiments, point registration module 316 receives direct input from the surgeon (e.g., in the form of a foot-pedal-press or the press of a dedicated button on the scope), where the CCU communicates this trigger through a custom interface to point registration module 316. In some embodiments, an output of point registration module 316 comprises a location of a tool tip when a measurement is initiated and/or terminated.

In some embodiments, the displacement aggregator module 317 receives real time updates to the location of the tool tip from point registration module 316. In some embodiments, displacement aggregator module 317 receives input from reference sizing module 314 or tool tracking module 306. For example, when point registration module 316 triggers a start of a measurement, displacement aggregator module 317 starts to track the displacement of the tool in pixels. This displacement may then be converted to units of distance such as millimeters or inches based on the instantaneous input received from reference sizing module 314. In some embodiments, the reference size in pixels varies based on a distance between a lens of the camera and the tooltip and/or optical properties of the camera. In some embodiments, displacement aggregator module 317 receives an end of measurement signal from point registration module 316 and stops accruing the distance measurement. Then, displacement aggregator module 317 may output the accrued distance as the measurement between a start point and an end point. In some embodiments, displacement aggregator module 317 sums the instantaneous displacements to compute a length of the path traced by a probe. In some embodiments, the frames connected to one another using the stitching module 318, as described herein, are provided to the xPand view module 321. The xPand view module 321 coordinate the stitched frames into a larger canvas to provide a wider surgical field of view. This expanded view of the surgical area can help an operator navigate the surgery more effectively. The expanded view may also allow the operator to visually track pathology, anatomical features, start point of a measurement, etc. that may be outside of the surgical field of view provided by the camera.

In some embodiments, the output from the landmark location module 320 is overlaid onto the video stream input from video stream input module 301 in a video blend module 312. In some embodiments, outputs from pathology measurement module 322 or xPand view module 321 are overlaid on the input from video stream input 301 in the blend module 312. The output from video blend module 312 may be displayed on an output 330 (e.g., a screen, a monitor, a TV, a laptop screen, etc.) The output from landmark location module 320 may be directed to the camera control unit to be scaled and overlaid onto the video stream of the procedure.

In some embodiments, an operator uses the systems and methods disclosed herein to measure a volume of an anatomical structure or a pathology during a surgery. In some embodiments, preoperative imaging data is used to measure the volume of the anatomical structure or the pathology. The preoperative imaging data may comprise diagnostic imaging. The preoperative imaging data may comprise MRI images or CT scan images. In some embodiments, the systems and methods disclosed herein comprise a module to ingest preoperative imaging data (e.g., MRI images or CT scan images). In some embodiments, an operator traces a line to select an area on an image (e.g., from a video stream of a surgery) during a surgery. The selected area may comprise an anatomical structure or pathology.

Figure 4:
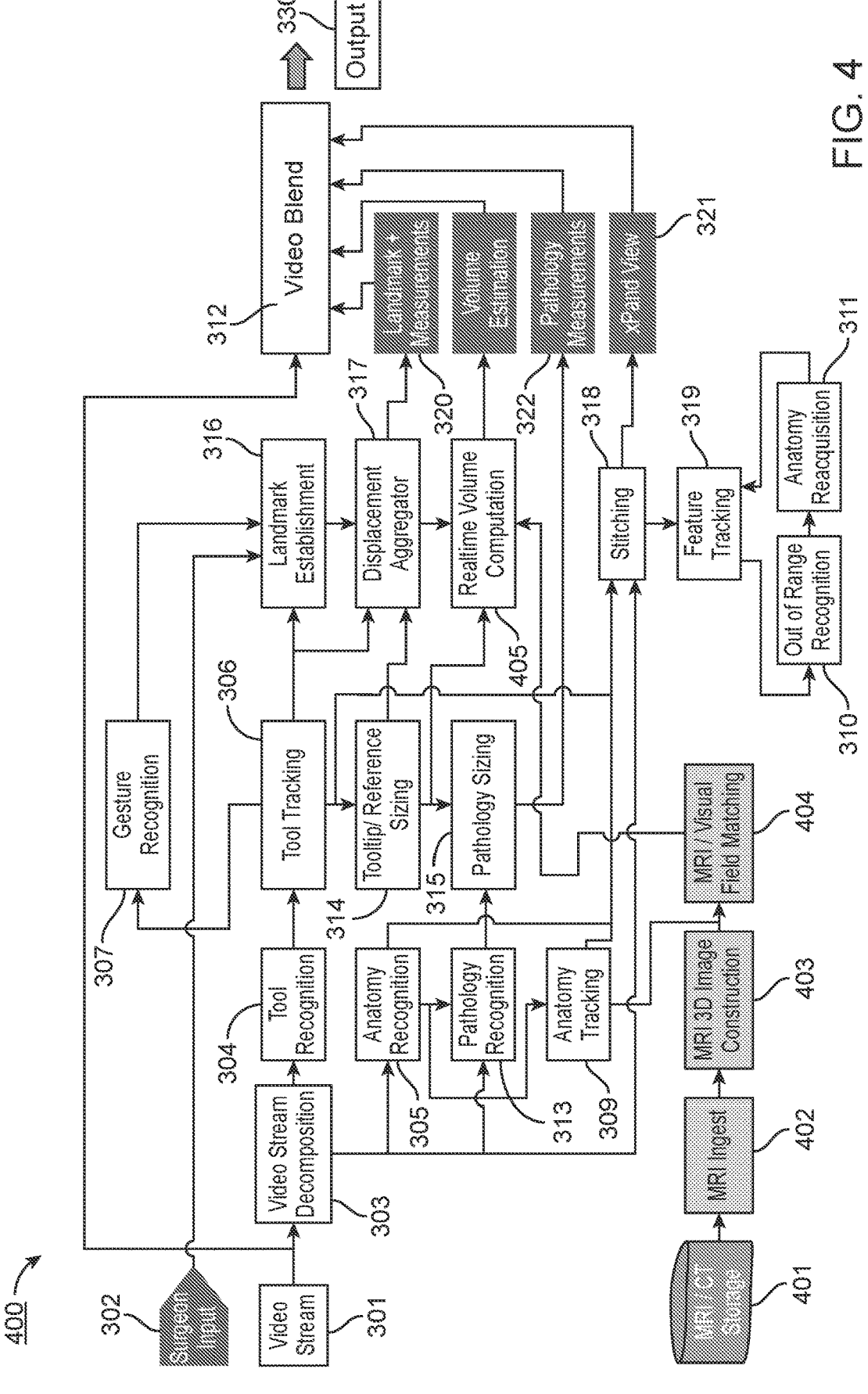
FIG. 4 shows a schematic of an exemplary workflow of measuring a volume of a selected area during an arthroscopic surgery, according to some embodiments.

FIG. 4 shows a schematic of an exemplary workflow of measuring a volume of a selected area during a surgery using preoperative imaging data. As shown in FIG. 4, a plurality of modules may be added to the system 300 shown in FIG. 3 to allow using preoperative medical imaging data 401 of a subject (e.g., radiology imaging data such as MRI or CT scan) to measure a volume of a selected on a video stream of an arthroscopic procedure from video stream input module 301. In some embodiments, a preoperative medical imaging ingest module 402 interfaces with an external repository to import the subject's preoperative medical imaging data 401. The preoperative medical imaging data may comprise radiological images of a subject. In some embodiments, the radiological images are from a joint of the subject. In some embodiments, the radiological images are associated with a shoulder, a knee, an ankle or a hip. In some embodiments, the radiological images are generated using magnetic resonance imaging (MRI), or computed tomography (CT) scanning. In some embodiments, MRI or CT scan images are acquired from the subject for an arthroscopic procedure (e.g., a knee surgery or a shoulder surgery). The MRI or CT scan images may comprise an image of a subject's knee or a shoulder. In some embodiments, MRI or CT scan images are obtained from the repository in a standard format (e.g., DICOM). In some embodiments, medical imaging ingest module 402 comprises an application programming interface (API) layer to abstract external system associated with an imaging system (e.g., MRI, or CT scan imaging) from the system 400. The output from medical imaging ingest module 402 may be provided to a three dimensional (3D) image reconstruction module 403. In some embodiments, 3D image reconstruction module 403 converts volumetric data in images from medical imaging ingest module 402 comprising one or more slices of two dimensional (2D) images and converts the data into a 3D image in a computer memory. In some embodiments, the coordinates of the selected area set by the operator are mapped onto the 3D image. In some embodiments, 3D image reconstruction module 403 may generate a multi-dimensional array comprising the 3D representation of a radiological image and the selected area mapped to the image. In some embodiments, the output from 3D image reconstruction module 403 may be merged with the mask(s) generated by the anatomy tracking module 309, using a mapping module 404. In some embodiments, mapping module 404 comprises a trained AI network to recognize anatomical structures in an image obtained preoperatively (e.g., an MRI or a CT scan image). In some embodiments, the anatomical structure may comprise a bony structure. In some embodiments, the anatomical structure may comprise a tendon. In some embodiments, the anatomical structure recognized in the image (e.g., an MRI or a CT scan image) may be masked (e.g., labeled) in mapping module 404 using the same labeling system used in anatomy recognition module 305. The anatomical structure recognized in mapping module 404 may then be matched to an anatomical structure recognized in anatomy recognition module 305. In some embodiments, the landmark specified in 3D image reconstruction module 403 may be mapped onto the anatomical structure recognized by anatomy recognition module 305. The mapping may be provided to a real-time volume computation module 405. In some embodiments, volume computation module 405 uses the output from mapping module 404 to compute a volume of the selected area set by an operator. In some embodiments, volume computation module 405 uses known scaling factors in the imaging formats and applies them to the masks of an anatomical structure or a pathology in the selected area to obtain a volume of the selected area, the anatomical structure, or the pathology. In some embodiments, an operator obtains partial volumes by indicating arbitrary lines or planes of dissections on an anatomical structure. In some embodiments, a measurement is used for bone-loss estimation. In some embodiments, a volume of bone-loss is measured using the systems and methods described herein. Imaging modalities (e.g., MRI) may produce images in which a voxel, (volumetric pixel), can represent a volume in physical space. Voxel sizes can range from about 0.5 to about 1.5 mm along two dimensions. The third dimension may be determined by the width of a slice which may be determined, for example, by the intended use of the MRI. Therefore, to map an MRI image, the anatomical structures may be matched in the MRI to those seen in the surgical field of view to determine the size of the anatomical structures.

For example, in a surgical procedure, a size (e.g., a dimension, or volume) of an anatomical structure, a pathology, or an organ may be measured. In some embodiments, the operator has to remove a portion of an anatomical structure (e.g., to remove a pathology, to reduce a size). During the surgical procedure, the operator provides an arbitrary line on, for example, an anatomical structure, where the arbitrary line indicates a dissection in the structure where the removal takes place. The system, as described herein, calculates a size of the anatomical structure based in part on a preoperative image (e.g., MRI or CT scan). The system may then calculate a size of a portion of the structure to be removed based in part on the dissection line. The system may estimate a shape of the portion being removed to estimate the size (e.g., volume) of the portion being removed. In some embodiments, to estimate a size of the anatomical structure and/or the portion of the anatomical structure being removed, the preoperative image (e.g., MRI or CT scan) is overlaid on the surgical field of view. Anatomy recognition modules (e.g., FIG. 4 anatomy recognition module 305), anatomy tracking module (e.g., FIG. 4 anatomy tracking module 309), and field matching module (e.g., FIG. 4 mapping module 404) may be used to overlay the images, as described herein. Upon mapping an anatomical structure in the two images (e.g., CT/MRI and surgical image), the images are scaled based at least on a size of each voxel in the preoperative image (e.g., MRI or CT Scan). Scaling may also be performed based at least in part on a size of a tool that may be recognized using a tool recognition module (e.g., FIG. 4 tool recognition module 304).

In some embodiments, landmark location module 320 is adjusted for the movement of the surgical camera. In some embodiments, when a similar structure is identified from a preoperative medical image (e.g., MRI or CT scan image) and from an image from a vide stream of the surgery, the two anatomical structures are matched (e.g., in mapping module 404), which corrects the frame for any image discrepancies associated with the surgical camera movement. In some embodiments, each frame from the video stream is corrected for the movement of the surgical camera.

Another aspect of the invention provides a method for expanding a field of view in a surgical video stream. According to an embodiment, the method may comprise: receiving a video stream captured by an imaging device; decomposing the video stream into a one or more images; processing the one or more images using at least one of a trained computer algorithm to (i) extract one or more image features, (ii) identify one or more anatomical structures; and generating a composite image to expand the field of view by matching the one or more images based on the extracted features or said identified anatomical structures.

In some embodiments, an imaging device comprises a lens of small focal length. In some embodiments, the focal length may be about 3 millimeters (mm) to about 5 mm, with about 30 degrees to about 90 degrees field of view. In some embodiments, the distance between the lens and the tissues in the region is in the order of a few centimeters. Therefore, a field of view seen by the operator (e.g., a surgeon) may be narrow. Thus, the operator may need to maintain a mental map of a region of surgery in order to orient themselves properly and see their action in the context of surrounding tissues. The narrow field of view may also limit the ability of the operator to perform measurements accurately. In some embodiments, an expanded field of view is generated by stitching a plurality of images captured by the imaging device. In some embodiments, the plurality of images is captured at different time points during a surgical procedure. In some embodiments, an operator performs a measurement, as described herein, across a one or more images using the expanded field of view.

Figure 5:
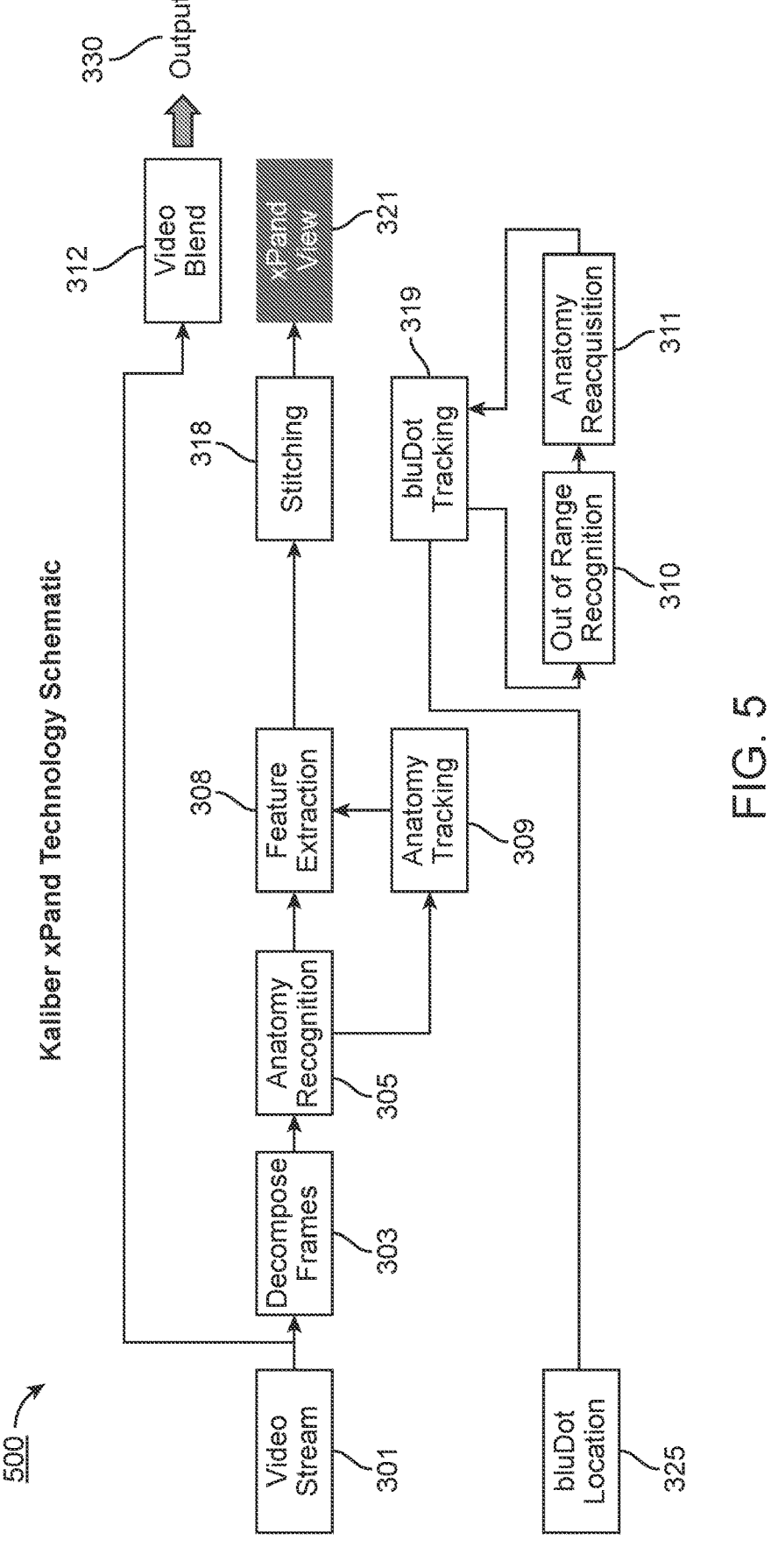
FIG. 5 shows a schematic of an exemplary workflow for generating an expanded field of view of an arthroscopic surgery, according to some embodiments.

FIG. 5 shows a schematic of an exemplary embodiment of a workflow for generating an expanded field of view, as described herein. The system 500 may comprise a plurality of modules which operate on the video stream input 301 generated by an arthroscopic camera. In some embodiments, video stream input 301 is processed by a video stream decomposition module 303 comprising a CV algorithm to decompose a video stream into a series of images. The series of images may be stored in a memory device. One or more images from the series of images may be provided to one or more downstream component comprising an anatomy recognition module 305. The output from anatomy recognition module 305 may then be sent to a feature extraction module 308 and/or an anatomy tracking module 309. In some embodiments, the anatomy tracking module 309 detects sets of coordinates of a location of an anatomical structure. In some embodiments, as the coordinates of an anatomical structure changes, anatomy tracking module 309 stores the previous coordinates in memory and updates the new sets of coordinates. In some embodiments, the feature extraction module 308 receives an input from anatomy recognition module 305 (e.g., an anatomy mask). In some embodiments, the feature extraction module 308 receives an input from a tool recognition module or a pathology module (e.g., a tool mask, or a pathology mask). In some embodiments, the feature extraction module 308 receives an input in a continuous manner. In some embodiments, the features (e.g., sets of distinct pixels) are extracted from the image. In some embodiments, the feature extraction module 308 uses an AI network to recognize a feature within an anatomical structure or a pathology in a field of view. Non-limiting examples of the AI network used in feature extraction module 308 may comprise Mask R-CNN, UNET, ResNET, YOLO, YOLO-2, or any combination thereof. In some embodiments, the AI networks are trained to recognize features (e.g., sets of distinct pixels) in an anatomical structure or a pathology. The features may comprise color, texture, curvature, discoloration, deformation of an anatomical structure. In some embodiments, the features (e.g., sets of distinct pixels) are recognized in comparison to surrounding features. In some embodiments, the AI networks are trained to extract a feature in an anatomical structure with respect to features recognized globally.

In some embodiments, feature extraction module 308 recognizes distinct anatomical structures and using these distinct anatomical structures to obtain globally distinct features. In some embodiments, a tool recognition mask is used by feature extraction module 308; the tool mask may be excluded from feature extraction or a recognized feature, as described herein. For example, an anatomical structure and feature points associated with the anatomical structure may be recognized. The anatomical structure may then be tracked. In some embodiments, a movement of the anatomical structure is also estimated. In some embodiments, a camera movement is inferred based in part on the anatomical structure movement. The feature points associated with the anatomical structure may be used to estimate the movement of the anatomical structure and therefor the camera. In some embodiments, the extracted feature along with the image frame associated with the feature are stored in a memory.

The information of the feature points is stored based on the anatomical structure they are associated with. In some embodiments, recognizing an anatomical structure in a field of view can trigger a set of feature points to be analyzed. The memory may be a buffer. A plurality of extracted features and their associated frames are sent to a stitching module 318.

A wider field of view may be generated using the stitching module 318 and the xPand view module 321, as described herein. This expanded view of the surgical area can help an operator navigate the surgery more effectively. An out of range recognition module 310 may be used to recognize a pathology, anatomical features, start point or end point of a measurement, etc. that may be located outside of the surgical field of view provided by the camera. An anatomy reacquisition module 311 may then be used to place the recognized feature or pathology, as mentioned herein, based at least in part on the recognized anatomical structure. This may allow the operator to make a measurement across two or more frames, where the frames are stitched together using the stitching module 318. The visual expanded view of the measurement may then be provided to the output 330 using the xPand View module 321. A feature tracking module 319 may be in communication with the out of range recognition module 310 and the anatomy reacquisition module 311 to assist those modules with tracking one or more features such as recognized anatomical structure(s). A location 325 of a point or mark of interest may be provided to the feature tracking module 319 so that the feature tracking module 319 may track this point or mark, for example, over time as it moves.

In some embodiments, a camera may move from the start point of the measurement to the endpoint of the measurement. As a result, the starting point may fall outside of the immediate field of view. In this case, the displacement may be computed continuously based at least in part on the recognized anatomical structures, as the field of view changes. For example, the algorithm may determine that a start point (e.g., landmark), 's' is 20 pixels to the right of a feature 'a' which is located on anatomical structure 'A'. As a new anatomical structure 'B' comes into view, a new feature point, 'b' may be acquired on the anatomical structure 'B'. Feature b's displacement from 'a' and accordingly from the starting point 's' may be computed. Similarly, as the anatomical structure 'A' disappears from the field of view, the location of 's' is tracked relative to 'b'. Similarly, as a new structure 'C' comes into the field of view, a new feature point 'c' may be acquired and its relative position from 'b' can be determined before the structure 'B' disappears. The position of the starting point is thus continuously tracked.

In some embodiments, the stitching module 318 arranges two or more frames by matching common features between the frames. In some embodiments, stitching module 318 uses the anatomy recognition masks match frames using organ boundaries to achieve proper matching of the frames. An expanded view may be generated by matching a plurality of frames as described herein. In some embodiments, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90, or 100 frames are matched to form an expanded view. In some embodiments, more than 100 frames are matched to form an expanded view. In some embodiments, about 20 frames to about 40 frames, about 30 frames to about 50 frames, about 25 frames to about 50 frames, or about 50 frames to about 100 frames are matched to form an expanded view. In some embodiments, a measurement may be performed across a plurality of frames in the expanded view, as described hereinbefore In some embodiments, a video stream from video stream input 301 (e.g., a real-time frame from the video stream) is placed in the center of the expanded view. In some embodiments, the expanded view is generated surrounding the real-time frame from the view stream from video stream input 301. In some embodiments, the expanded view and the video stream are overlaid and displayed on a monitor 30.

Computer Systems

Figure 6:
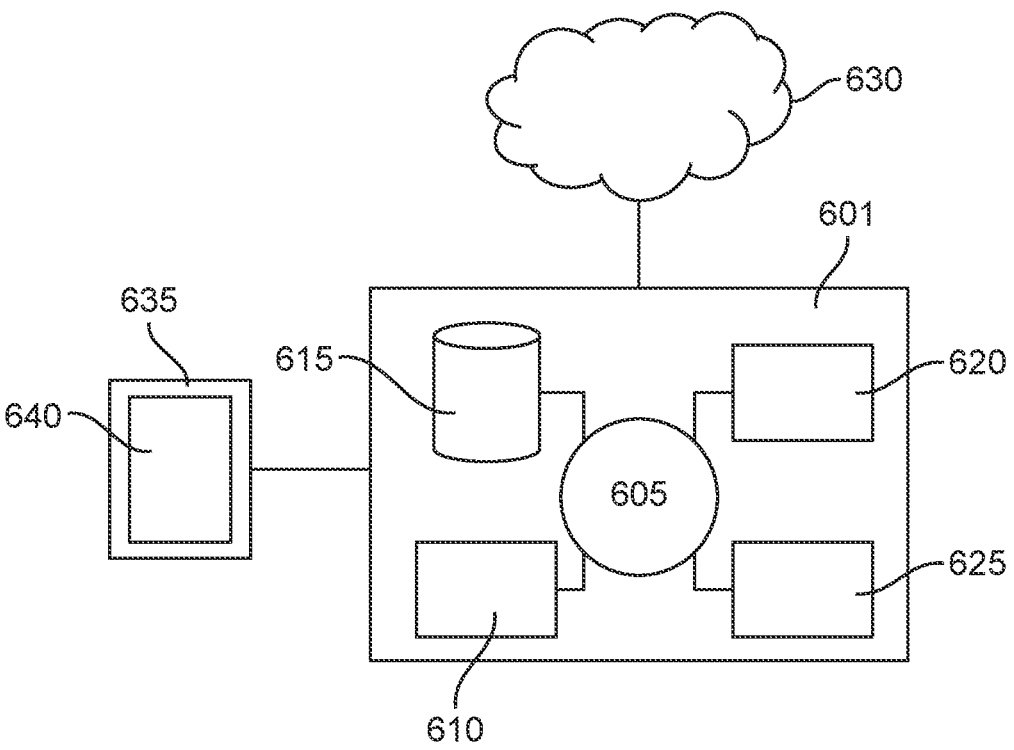
FIG. 6 shows a computer system that is programmed or otherwise configured to implement methods provided herein, according to some embodiments.

The present invention provides computer systems that are programmed to implement methods of the disclosure. FIG. 6 shows a computer system 601 that is programmed or otherwise configured to perform one or more functions or operations of methods of the present disclosure. The computer system 601 can regulate various aspects of the present disclosure, such as, for example, of receiving an image from an interventional imaging device, identifying features in the image using an image recognition algorithm, overlaying the features on a video feed on a display device, registering a start location and an end location for a measurement, estimate a measurement, provide a measurement, make recommendations or suggestion to an operator based on the identified features in the image. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, readonly memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some embodiments is a telecommunication and/or data network. The network 630 can include one or more computer servers, which can enable distributed computing, such as cloud computing. The network 630, in some embodiments with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some embodiments, the circuit is an application specific integrated circuit (ASIC).

The storage unit 615 can store files, such as drivers, libraries and saved programs. The storage unit 615 can store user data, e.g., user preferences and user programs. The computer system 601 in some embodiments can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user (e.g., a portable computer, a tablet, a smart display device, a smart tv, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some embodiments, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, an overlay of the identified features on a video feed from an arthroscope or to provide a measurement to an operator in the course of a surgery. Examples of UI's include, without limitation, a graphical user interface (GUI) and web-based user interface.

Methods and systems of the present invention can be implemented by way of one or more algorithms. An algorithm can be implemented by way of software upon execution by the central processing unit 605. The algorithm can, for example, receiving an image from an interventional imaging device, identifying a feature in the image using an image recognition algorithm, overlaying the features on a video feed on a display device, registering a start location and an end location for a measurement, provide a measurement to an operator based on the identified feature and/or a selected point, path or area in the image.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be further understood that various alternatives to the embodiments of the invention described herein may be employed in practicing the invention. Accordingly, it should be understood that the invention covers various alternatives, modifications, variations or equivalents to the embodiments of the invention described herein.

Also, elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Further, embodiments of the invention specifically contemplate the exclusion of an element, act, or characteristic, etc. when that element, act or characteristic is positively recited. Hence, the scope of the present invention is not limited to the specifics of the described embodiments but is instead limited solely by the appended claims.

What is claimed is:

1. A system for guiding a minimally invasive procedure, the system comprising one or more computer processors and one or more non-transitory computer-readable storage media storing instructions that are operable, when executed by said one or more computer processors, to cause said one or more computer processors to perform operations comprising:

receiving a video stream captured by an imaging device;

processing said video stream using processing modules including: a tool recognition module, a tooltip reference sizing module, an anatomy recognition module, and a tool tracking module, wherein said processing comprises:

identifying a surgical tool and one or more elements in said video stream, wherein said one or more elements comprises one or more of an anatomical structure, an operational procedure or action, or a pathology; and labeling said identified one or more elements in said video stream;

receiving an indication from an operator to select one or more of a plurality of points or an area in said video stream;

calculating one or more measurements for said selected area in said video stream; wherein said one or more measurements comprise one or more of a length, a surface area, a circumference, or a volume, further wherein said tooltip reference sizing module estimates a size of tooltip of said identified surgical tool using a trained machine learning algorithm, and wherein a pathology sizing module estimates a size of said identified pathology based at least partially on said estimated size of tooltip; and displaying said measurements on a displaying device intraoperatively to be used by an operator during said arthroscopic procedure.

2. The system of claim 1, wherein said processing modules further include one or more of: a video stream decomposition module, a gesture recognition module, a landmark establishment module, a distance aggregator module, a video blend module, a pathology detection module, a pathology sizing module, or a radiology imaging module.

3. The system of claim 2, wherein said processing modules each comprise one or more trained machine learning algorithms.

4. The system of claim 3, wherein each trained machine learning algorithm is a neural network.

5. The system of claim 2, wherein said video stream decomposition module decomposes said video stream into a series of images.

6. The system of claim 5, wherein said series of images are stored in a memory device.

7. The system of claim 2, wherein said radiological imaging module comprises: a radiology ingest module, a three-dimensional image construction module, a visual field mapping module, a real-time volume computation module.

8. The system of claim 7, wherein said radiology ingest module interfaces with an external repository to import a subject's radiological imagery.

9. The system of claim 8, wherein said radiological imagery comprises one or more of magnetic resonance imaging (MRI), computed tomography (CT) scanning, ultrasound, or a combination thereof.

10. The system of claim 8, said radiological imagery includes an image of a landmark.

11. The system of claim 8, said radiological imagery comprises volumetric data.

12. The system of claim 11, a three-dimensional image reconstruction module generates a three-dimensional object from said volumetric radiological imagery.

13. The system of claim 12, said three-dimensional image reconstruction module further generates coordinates to map said landmark onto said three-dimensional object.

14. The system of claim 1, wherein said labeling said video stream further comprises displaying a shape outline surrounding said one or more elements.

15. The system of claim 1, wherein said operator uses a standard surgical probe to select said area in said video stream.

16. The system of claim 1, wherein calculating one or more measurements comprises calculating a distance between a first point and a second point.

17. The system of claim 16, wherein at least one of said first point or said second point moves outside of said field of view.

18. The system of claim 1, wherein calculating said one or more measurements for said selected area comprises performing a volume calculation, wherein said volume calculation comprises:

receiving a three dimensional radiology image of a subject;

receiving an indication from an operator to select at least one element from said one or more elements in said video stream; and calculating a volume of said selected area based at least partially on the selected at least one element on the three dimensional radiological image.

19. The system of claim 18, wherein receiving the indication of the operator to select said at least one element from said or more elements in said video stream comprises receiving an outline of a selected area from the operator.

20. The system of claim 1, wherein said operations further comprise:

generating an overlay video stream by blending said labels or said measurements with said received video stream; and displaying said overlaid video stream on a displaying device.

\* \* \* \* \*